United States Patent [19]

Cochran

[11] Patent Number: 5,451,499

[45] Date of Patent: Sep. 19, 1995

[54] ATTENUATED, GENETICALLY-ENGINEERED PSEUDORABIES VIRUS S-PRV-155 AND USES THEREOF

[75] Inventor: Mark D. Cochran, Carlsbad, Calif.

[73] Assignee: Syntro Corporation, Lenexa, Kans.

[21] Appl. No.: 55,530

[22] Filed: Apr. 30, 1993

Related U.S. Application Data

[62] Division of Ser. No. 663,413, Mar. 1, 1991, Pat. No. 5,240,703.

[51] Int. Cl.⁶ ........................ C12Q 1/70; C12N 15/00; C12N 7/00; A61K 39/12
[52] U.S. Cl. ...................................... 435/5; 424/229.1; 424/205.1; 435/172.1; 435/172.3; 435/235.1; 435/7.1
[58] Field of Search ............ 424/89; 435/172.1, 172.3, 435/235.1, 7.1, 236, 5

*Primary Examiner*—Christine M. Nucker
*Assistant Examiner*—L. F. Smith
*Attorney, Agent, or Firm*—John P. White

[57] ABSTRACT

The present invention provides an attenuated, genetically-engineered pseudorabies virus designated S-PRY-155 (ATCC Accession No. VR 2311). A vaccine is provided which comprises an effective immunizing amount of S-PRY-155 and a suitable carrier. A method of immunizing an animal against disease caused by pseudorabies virus is also provided which comprises administering to the animal an effective immunizing dose of the vaccine. The present invention also provides a method for distinguishing an animal vaccinated with the vaccine of the present invention from an animal infected with a naturally-occurring, wild-type pseudorabies virus.

8 Claims, 13 Drawing Sheets

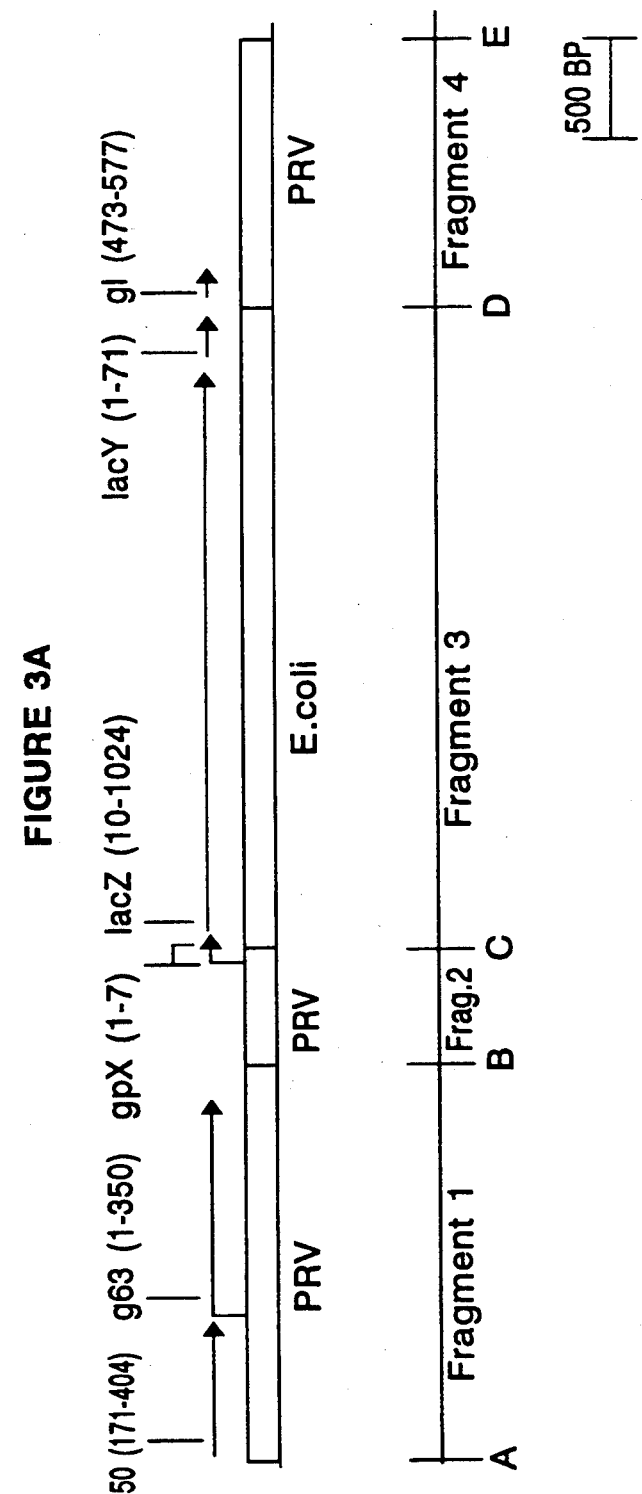

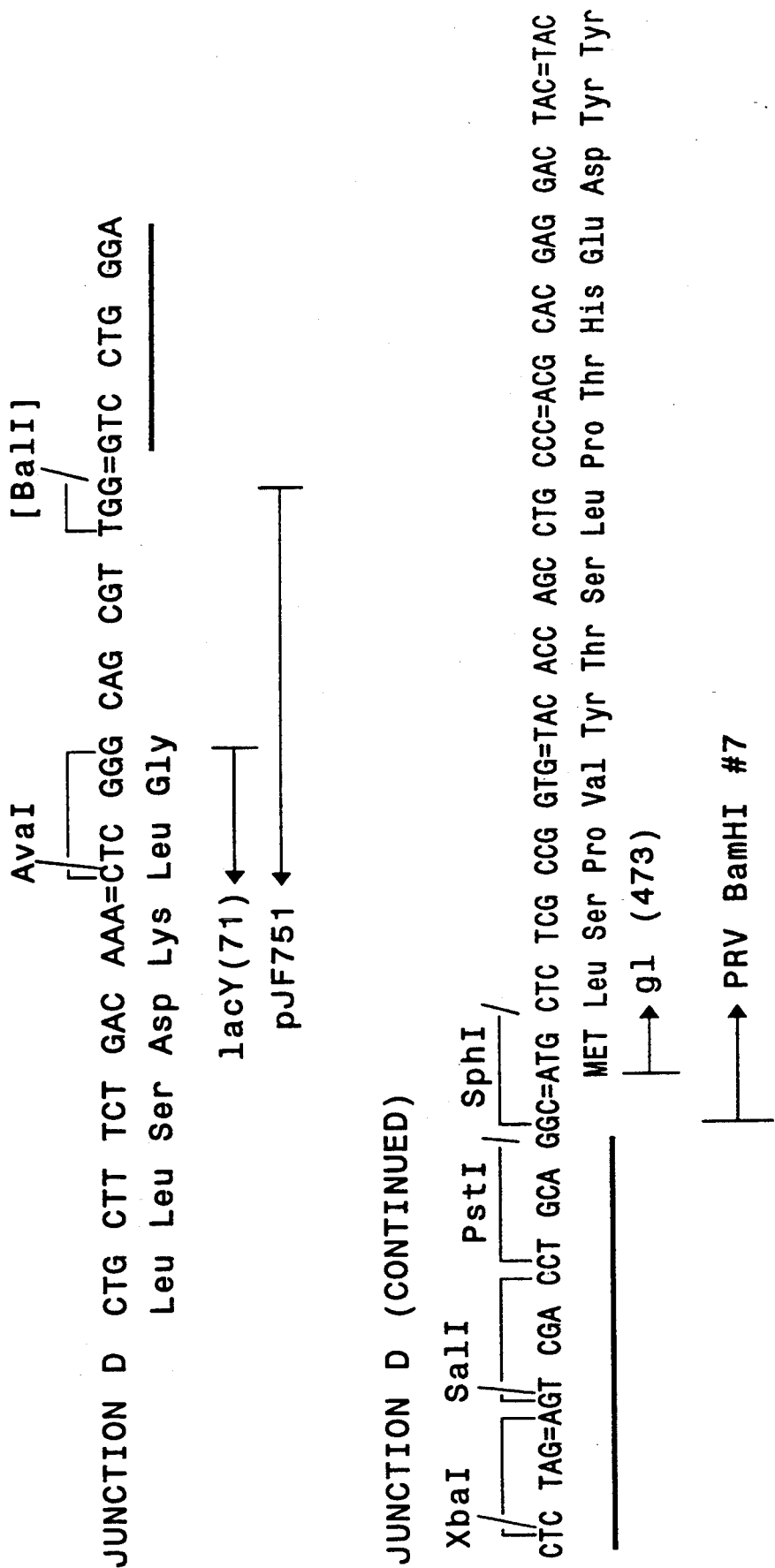

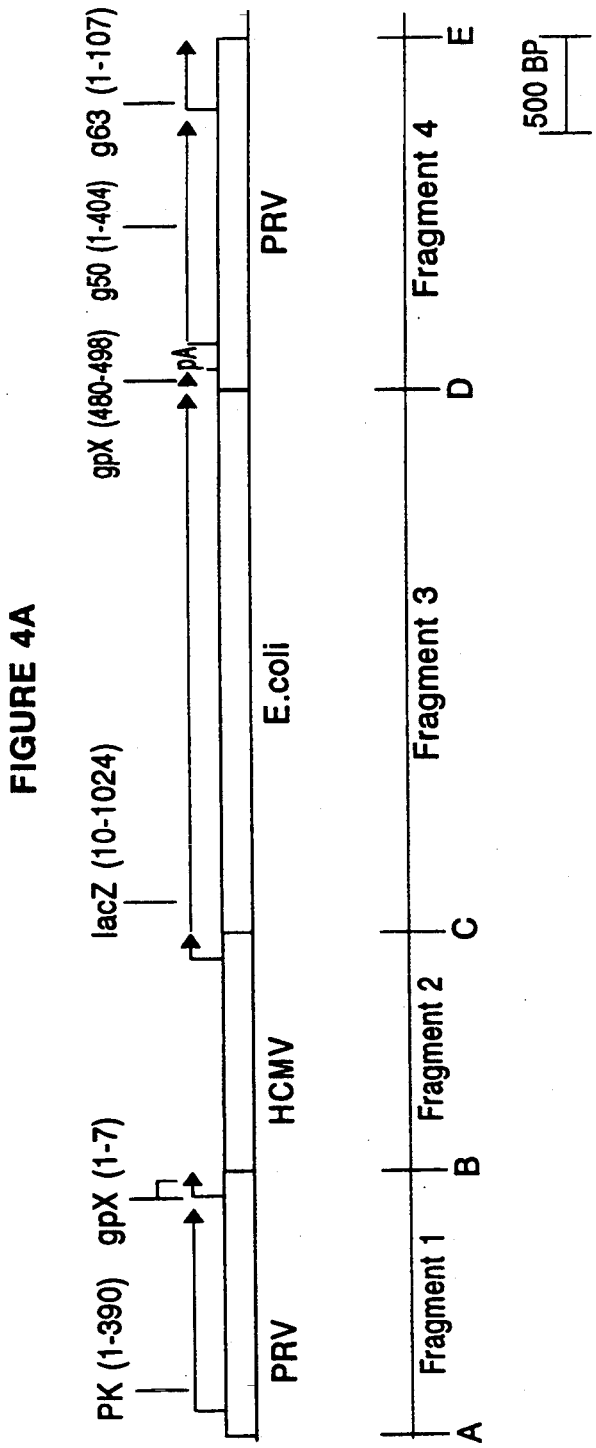

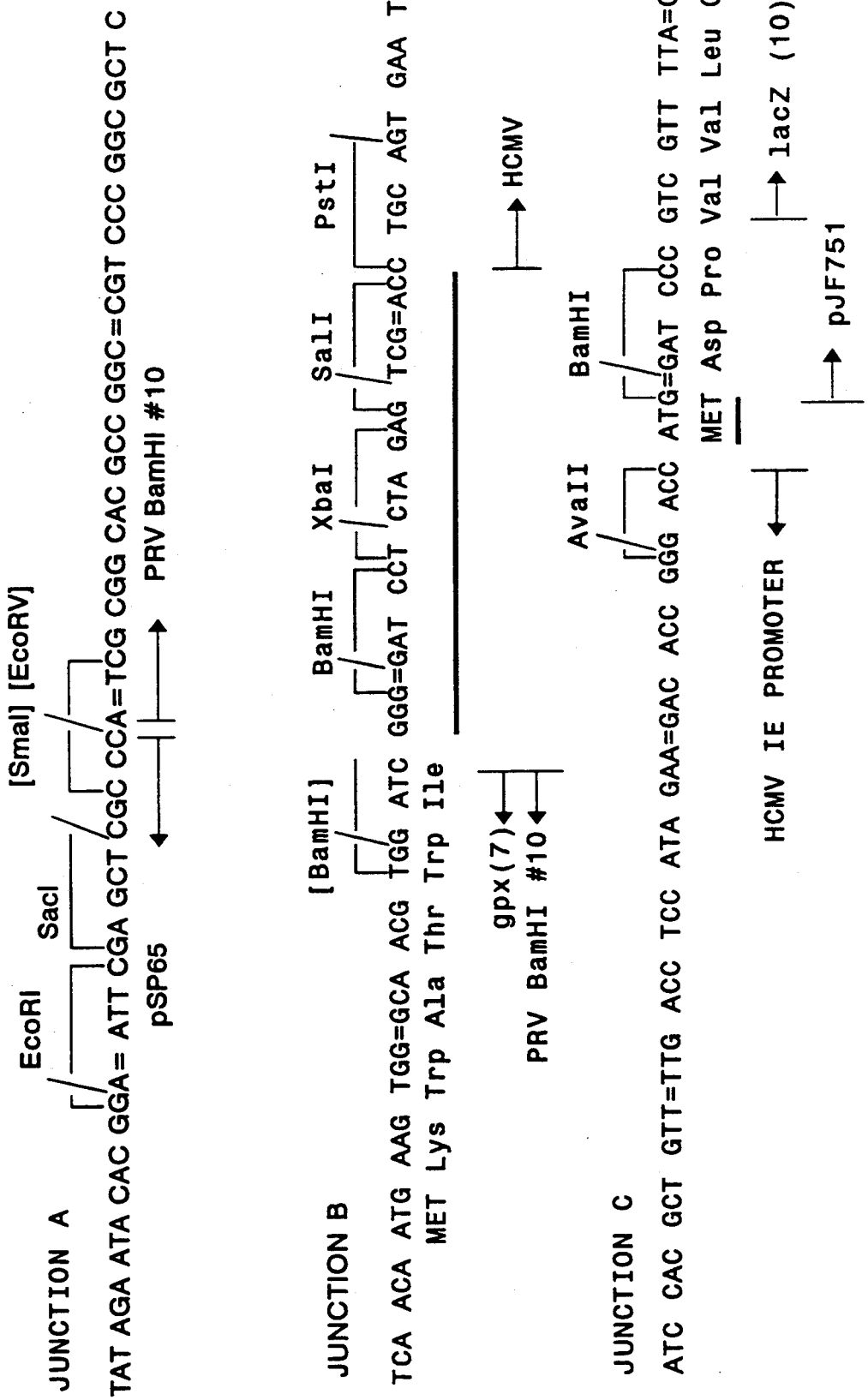

FIGURE 4C

JUNCTION D

```
                                                          PvuII
TGG AGC CCG TCA GTA=TCG GCG GAA TTA CAG=CTG AGC GCC GGT CGC=TAC CAT TAC CAG
Trp Ser Pro Ser Val Ser Ala Glu Leu Gln Leu Ser Ala Gly Arg Tyr His Tyr Gln
                                    ├──pJF751
                                      XbaI
```

JUNCTION D (CONTINUED)

```
                     BglII
TTG=GTC TGG TGT CAA AAA=GAT CTA GAA TAA GCT=AGA GGA TCG ATC CCC=TAT GGC GAT
Leu Val Trp Cys Gln Lys Asp Leu Glu ---
├──lacZ (1024)         [NdeI]
```

JUNCTION D (CONTINUED)

```
CAT CAG=GGC CCG ATC CCC TAT=GGC GAT CAT CAG GGC=CCG GGC CCG GAA
                        Me tAl aIl eIl eAr gAl aAr gAl aAr gAs
                        ──▶ gpX(480)
                            ──▶ PRV BamHI #7
```

JUNCTION D (CONTINUED)

```
CGA=CGG CTA CCG CCA CGT=GGC CTC CGC CTG ACC=CGG CCC CGC CCG ACT=CCC CCG
nAs pGL yTy rAr gHi sVa lAl aSe rAl a-- -
```

JUNCTION E

GAG TAC GAC CTC TGC=CCC CGC GTG CAC CAC=GAG GCT GCA TTA ATG=AAT CGG CCA ACG C
Glu Tyr Asp Leu Cys Pro Arg Val His His Glu Ala Ala Leu Met Asn Arg Pro Thr

[StuI]  [PvuII]

g63 (107)

PRV BamHI #7 → pSP65

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:1:

```
TATAGAATAC ACGGAATTCG AGCTCGCCCA TCGCGGCACG CCGGCCGTCC CGGCGCT    57
```

( 2 ) INFORMATION FOR SEQ ID NO:2:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..57
        ( D ) OTHER INFORMATION:

( x i ) SEQUENCE DESCRIPTION: SEQ ID NO:2:

```
GCG  CGC  GAC  GCG  TAC  GAC  ACC  AAG  GTC  GAC  TCT  AGA  GTC  GAC  GTC  TGG    48
Ala  Arg  Asp  Ala  Tyr  Asp  Thr  Lys  Val  Asp  Ser  Arg  Val  Asp  Val  Trp
 1              5                        10                       15

GGC  GCG  GGG                                                                      57
Gly  Ala  Gly
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Ala  Arg  Asp  Ala  Tyr  Asp  Thr  Lys  Val  Asp  Ser  Arg  Val  Asp  Val  Trp
 1              5                        10                       15

Gly  Ala  Gly
```

( 2 ) INFORMATION FOR SEQ ID NO:4:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( i x ) FEATURE:
    ( A ) NAME/KEY: CDS
    ( B ) LOCATION: 13..57
    ( D ) OTHER INFORMATION:

( x i ) SEQUENCE DESCRIPTION: SEQ ID NO:4:

```
CACAGCTCAA CA ATG AAG TGG GCA ACG TGG ATC GAT CCC GTC GTT TTA        48
              Met Lys Trp Ala Thr Trp Ile Asp Pro Val Val Leu
               1           5                      10

CAA CGT CGT                                                           57
Gln Arg Arg
         15
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Lys Trp Ala Thr Trp Ile Asp Pro Val Val Leu Gln Arg Arg
 1           5                      10                   15
```

( 2 ) INFORMATION FOR SEQ ID NO:6:

( i ) SEQUENCE CHARACTERISTICS:
        ( A ) LENGTH: 107 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..9
        ( D ) OTHER INFORMATION:

( i x ) FEATURE:
        ( A ) NAME/KEY: CDS
        ( B ) LOCATION: 48..104
        ( D ) OTHER INFORMATION:

( x i ) SEQUENCE DESCRIPTION: SEQ ID NO:6:

```
AAA CTC GGG CAGCGTTGGG TCCTGGGACT CTAGAGGATC GATCCCCT ATG GCG        53
Lys Leu Gly                                            Met Ala
 1                                                      1

ATC ATC AGG GCC CGG GCC CGG AAC GAC GGC TAC CGC CAC GTG GCC TCC    101
Ile Ile Arg Ala Arg Ala Arg Asn Asp Gly Tyr Arg His Val Ala Ser
         5                      10                  15

GCC TGA                                                             107
Ala
```

( 2 ) INFORMATION FOR SEQ ID NO:7:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Lys Leu Gly
 1

( 2 ) INFORMATION FOR SEQ ID NO:8:

( i ) SEQUENCE CHARACTERISTICS:
          ( A ) LENGTH: 19 amino acids
          ( B ) TYPE: amino acid
          ( D ) TOPOLOGY: linear ( i i ) MOLECULE TYPE: protein ( x i ) SEQUENCE DESCRIPTION: SEQ ID NO:8:

Met Ala Ile Ile Arg Ala Arg Ala Arg Asn Asp Gly Tyr Arg His Val
 1               5                   10                  15
Ala Ser Ala ( 2 ) INFORMATION FOR SEQ ID NO:9:

( i ) SEQUENCE CHARACTERISTICS:
          ( A ) LENGTH: 107 base pairs
          ( B ) TYPE: nucleic acid
          ( C ) STRANDEDNESS: double
          ( D ) TOPOLOGY: circular ( i i ) MOLECULE TYPE: DNA (genomic)

( i i i ) HYPOTHETICAL: N ( i v ) ANTI-SENSE: N ( i x ) FEATURE:
          ( A ) NAME/KEY: CDS
          ( B ) LOCATION: 1..9
          ( D ) OTHER INFORMATION:

( i x ) FEATURE:
          ( A ) NAME/KEY: CDS
          ( B ) LOCATION: 48..104
          ( D ) OTHER INFORMATION:

( x i ) SEQUENCE DESCRIPTION: SEQ ID NO:9:

```
AAA CTC GGG CAGCGTTGGG TCCTGGGACT CTAGAGGATC GATCCCCT ATG GCG      53
Lys Leu Gly                                            Met Ala
 1                                                      1

ATC ATC AGG GCC CGG GCC CGG AAC GAC GGC TAC CGC CAC GTG GCC TCC  101
Ile Ile Arg Ala Arg Ala Arg Asn Asp Gly Tyr Arg His Val Ala Ser
         5                   10                  15

GCC TGA                                                           107
Ala
```

( 2 ) INFORMATION FOR SEQ ID NO:10:

( i ) SEQUENCE CHARACTERISTICS:
          ( A ) LENGTH: 3 amino acids
          ( B ) TYPE: amino acid
          ( D ) TOPOLOGY: linear ( i i ) MOLECULE TYPE: protein ( x i ) SEQUENCE DESCRIPTION: SEQ ID NO:10:

Lys Leu Gly
 1

( 2 ) INFORMATION FOR SEQ ID NO:11:

( i ) SEQUENCE CHARACTERISTICS:

(A) LENGTH: 19 amino acids
(B) TYPE: amino acid
(D) TOPOLOGY: linear (i i) MOLECULE TYPE: protein (x i) SEQUENCE DESCRIPTION: SEQ ID NO:11:

Met Ala Ile Ile Arg Ala Arg Ala Arg Asn Asp Gly Tyr Arg His Val
 1               5                  10                  15
Ala Ser Ala (2) INFORMATION FOR SEQ ID NO:12:

(i) SEQUENCE CHARACTERISTICS:
        (A) LENGTH: 57 base pairs
        (B) TYPE: nucleic acid
        (C) STRANDEDNESS: double
        (D) TOPOLOGY: circular (i i) MOLECULE TYPE: DNA (genomic)

(i i i) HYPOTHETICAL: N (i v) ANTI-SENSE: N (i x) FEATURE:
        (A) NAME/KEY: CDS
        (B) LOCATION: 1..33
        (D) OTHER INFORMATION:

(x i) SEQUENCE DESCRIPTION: SEQ ID NO:12:

GAG TAC GAC CTC TGC CCC CGC GTG CAC CAC GAG GCTGCATTAA TGAATCGGCC      53
Glu Tyr Asp Leu Cys Pro Arg Val His His Glu
 1               5                  10
AACG                                                                   57

(2) INFORMATION FOR SEQ ID NO:13:

(i) SEQUENCE CHARACTERISTICS:
        (A) LENGTH: 11 amino acids
        (B) TYPE: amino acid
        (D) TOPOLOGY: linear (i i) MOLECULE TYPE: protein (x i) SEQUENCE DESCRIPTION: SEQ ID NO:13:

Glu Tyr Asp Leu Cys Pro Arg Val His His Glu
 1               5                  10

(2) INFORMATION FOR SEQ ID NO:14:

(i) SEQUENCE CHARACTERISTICS:
        (A) LENGTH: 57 base pairs
        (B) TYPE: nucleic acid
        (C) STRANDEDNESS: double
        (D) TOPOLOGY: circular (i i) MOLECULE TYPE: DNA (genomic)

(i i i) HYPOTHETICAL: N (i v) ANTI-SENSE: N (i x) FEATURE:
        (A) NAME/KEY: CDS
        (B) LOCATION: 31..57
        (D) OTHER INFORMATION:

(x i) SEQUENCE DESCRIPTION: SEQ ID NO:14:

ACCATGATTA CGAATTCGAG CTCGGTACCC GAC GGC GTG AAC ATC CTC ACC GAC       54
                                 Asp Gly Val Asn Ile Leu Thr Asp
                                  1               5

```
GAC                                                                                      57
Asp
```

( 2 ) INFORMATION FOR SEQ ID NO:15:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: protein ( x i ) SEQUENCE DESCRIPTION: SEQ ID NO:15:

```
Asp  Gly  Val  Asn  Ile  Leu  Thr  Asp  Asp
 1               5
```

( 2 ) INFORMATION FOR SEQ ID NO:16:

( i ) SEQUENCE CHARACTERISTICS:
    ( A ) LENGTH: 57 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:16:

```
TTATCTCCGT  CCGCGCCGTT  TTGGGGATCC  TCTAGAGTCG  ACGTCTGGGG  CGCGGGG          57
```

( 2 ) INFORMATION FOR SEQ ID NO:17:

( i ) SEQUENCE CHARACTERISTICS:
    ( A ) LENGTH: 57 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: N ( i v ) ANTI-SENSE: N ( i x ) FEATURE:
    ( A ) NAME/KEY: CDS
    ( B ) LOCATION: 13..57
    ( D ) OTHER INFORMATION:

( x i ) SEQUENCE DESCRIPTION: SEQ ID NO:17:

```
CACAGCTCAA CA ATG AAG TGG GCA ACG TGG ATC GAT CCC GTC GTT TTA           48
              Met Lys Trp Ala Thr Trp Ile Asp Pro Val Val Leu
               1               5                       10

CAA CGT CGT                                                              57
Gln Arg Arg
         15
```

( 2 ) INFORMATION FOR SEQ ID NO:18:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: protein ( x i ) SEQUENCE DESCRIPTION: SEQ ID NO:18:

```
Met  Lys  Trp  Ala  Thr  Trp  Ile  Asp  Pro  Val  Val  Leu  Gln  Arg  Arg
 1                   5                        10                       15
```

( 2 ) INFORMATION FOR SEQ ID NO:19:

( i ) SEQUENCE CHARACTERISTICS:
        ( A ) LENGTH: 108 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..21
        ( D ) OTHER INFORMATION:

( i x ) FEATURE:
        ( A ) NAME/KEY: CDS
        ( B ) LOCATION: 61..108
        ( D ) OTHER INFORMATION:

( x i ) SEQUENCE DESCRIPTION: SEQ ID NO:19:

```
CTG CTT TCT GAC AAA CTC GGG CAGCGTTGGG TCCTGGGACT CTAGAGTCGA       51
Leu Leu Ser Asp Lys Leu Gly
 1               5

CCTGCAGGC ATG CTC TCG CCG GTG TAC ACC AGC CTG CCC ACG CAC GAG      99
          Met Leu Ser Pro Val Tyr Thr Ser Leu Pro Thr His Glu
           1           5                   10

GAC TAC TAC                                                       108
Asp Tyr Tyr
 15
```

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Leu Leu Ser Asp Lys Leu Gly
 1               5
```

( 2 ) INFORMATION FOR SEQ ID NO:21:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met Leu Ser Pro Val Tyr Thr Ser Leu Pro Thr His Glu Asp Tyr Tyr
 1               5                   10                  15
```

( 2 ) INFORMATION FOR SEQ ID NO:22:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:22:

ACACGGAGTG GTCCTCCGTC ATCAACGGGA TCCCCGGGCG AGCTCGAATT CCGTGTA    57

( 2 ) INFORMATION FOR SEQ ID NO:23:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:23:

TATAGAATAC ACGGAATTCG AGCTCGCCCA TCGCGGCACG CCGGCCGTCC CGGCGCTC    58

( 2 ) INFORMATION FOR SEQ ID NO:24:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 7..27
        ( D ) OTHER INFORMATION:

( x i ) SEQUENCE DESCRIPTION: SEQ ID NO:24:

```
TCAACA ATG AAG TGG GCA ACG TGG ATC GGGGATCCTC TAGAGTCGAC            47
       Met Lys Trp Ala Thr Trp Ile
        1               5

CTGCAGTGAA T                                                        58
```

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met Lys Trp Ala Thr Trp Ile
 1               5
```

( 2 ) INFORMATION FOR SEQ ID NO:26:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( i x ) FEATURE:
    ( A ) NAME/KEY: CDS
    ( B ) LOCATION: 40..58
    ( D ) OTHER INFORMATION:

( x i ) SEQUENCE DESCRIPTION: SEQ ID NO:26:

```
ATCCACGCTG TTTTGACCTC CATAGAAGAC ACCGGGACC ATG GAT CCC GTC GTT      54
                                            Met Asp Pro Val Val
                                            1               5

TTA C                                                               58
Leu
```

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Met Asp Pro Val Val Leu
1               5
```

( 2 ) INFORMATION FOR SEQ ID NO:28:

( i ) SEQUENCE CHARACTERISTICS:
        ( A ) LENGTH: 216 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..84
        ( D ) OTHER INFORMATION:

( i x ) FEATURE:
        ( A ) NAME/KEY: CDS
        ( B ) LOCATION: 134..190
        ( D ) OTHER INFORMATION:

( x i ) SEQUENCE DESCRIPTION: SEQ ID NO:28:

```
TGG AGC CCG TCA GTA TCG GCG GAA TTA CAG CTG AGC GCC GGT CGC TAC      48
Trp Ser Pro Ser Val Ser Ala Glu Leu Gln Leu Ser Ala Gly Arg Tyr
1               5                   10                  15

CAT TAC CAG TTG GTC TGG TGT CAA AAA GAT CTA GAA TAAGCTAGAG           94
His Tyr Gln Leu Val Trp Cys Gln Lys Asp Leu Glu
            20                  25

GATCGATCCC CTATGGCGAT CATCAGGGCC CGATCCCCT ATG GCG ATC ATC AGG       148
                                            Met Ala Ile Ile Arg
                                            1               5

GCC CGG GCC CGG AAC GAC GGC TAC CGC CAC GTG GCC TCC GCC              190
Ala Arg Ala Arg Asn Asp Gly Tyr Arg His Val Ala Ser Ala
            10                  15

TGACCCGGCC CCGCCCGACT CCCCCG                                        216
```

( 2 ) INFORMATION FOR SEQ ID NO:29:

( i ) SEQUENCE CHARACTERISTICS:
        ( A ) LENGTH: 28 amino acids
        ( B ) TYPE: amino acid
        ( D ) TOPOLOGY: linear -continued (ii) MOLECULE TYPE: protein (xi) SEQUENCE DESCRIPTION: SEQ ID NO:29:

Trp Ser Pro Ser Val Ser Ala Glu Leu Gln Leu Ser Ala Gly Arg Tyr
1               5                   10                  15

His Tyr Gln Leu Val Trp Cys Gln Lys Asp Leu Glu
            20              25

(2) INFORMATION FOR SEQ ID NO:30:

(i) SEQUENCE CHARACTERISTICS:
      (A) LENGTH: 19 amino acids
      (B) TYPE: amino acid
      (D) TOPOLOGY: linear (ii) MOLECULE TYPE: protein (xi) SEQUENCE DESCRIPTION: SEQ ID NO:30:

Met Ala Ile Ile Arg Ala Arg Ala Arg Asn Asp Gly Tyr Arg His Val
1               5                   10                  15

Ala Ser Ala (2) INFORMATION FOR SEQ ID NO:31:

(i) SEQUENCE CHARACTERISTICS:
      (A) LENGTH: 58 base pairs
      (B) TYPE: nucleic acid
      (C) STRANDEDNESS: double
      (D) TOPOLOGY: circular (ii) MOLECULE TYPE: DNA (genomic)

(iii) HYPOTHETICAL: N (iv) ANTI-SENSE: N (ix) FEATURE:
      (A) NAME/KEY: CDS
      (B) LOCATION: 1..33
      (D) OTHER INFORMATION:

(xi) SEQUENCE DESCRIPTION: SEQ ID NO:31:

GAG TAC GAC CTC TGC CCC CGC GTG CAC CAC GAG GCTGCATTAA TGAATCGGCC    53
Glu Tyr Asp Leu Cys Pro Arg Val His His Glu
1             5                   10

AACGC    58

(2) INFORMATION FOR SEQ ID NO:32:

(i) SEQUENCE CHARACTERISTICS:
      (A) LENGTH: 11 amino acids
      (B) TYPE: amino acid
      (D) TOPOLOGY: linear (ii) MOLECULE TYPE: protein (xi) SEQUENCE DESCRIPTION: SEQ ID NO:32:

Glu Tyr Asp Leu Cys Pro Arg Val His His Glu
1               5                   10

ATTENUATED, GENETICALLY-ENGINEERED PSEUDORABIES VIRUS S-PRV-155 AND USES THEREOF

This application is a divisional application of U.S. Ser. No. 663,413, filed Mar. 1, 1991, now U.S. Pat. No. 5,240,703.

Within this application several publications are referenced by arabic numerals within parentheses. Full citations for these references may be found at the end of the specification immediately preceding the claims. The disclosures of these publications in their entireties are hereby incorporated by reference into this application in order to more fully describe the state of the art to which this invention pertains.

FIELD OF THE INVENTION

The present invention involves an attenuated pseudorabies virus useful in a live virus vaccine to protect swine from pseudorabies. The invention further involves the use of such a virus to permit one to distinguish between an animal which has been vaccinated with the virus and an animal infected by wild-type pseudorabies virus.

BACKGROUND OF THE INVENTION

The ability to isolate viral DNA and clone this isolated DNA into bacterial plasmids has greatly expanded the approaches available to make viral vaccines. The methods used to make the present invention involve modifying cloned vital DNA sequences by insertions, deletions and single or multiple base changes. The modified DNA is then reinserted into the viral genome to render the virus non-pathogenic. The resulting live virus may then be used in a vaccine to elicit an immune response in a host animal and to protect the animal against a disease.

One group of animal viruses, the herpesviruses or Herpetoviridae, is an example of a class of viruses amenable to this approach. These viruses contain 100,000 to 200,000 base pairs of DNA as their genetic material. Importantly, several regions of the genome have been identified that are nonessential for the replication of virus in vitro in cell culture. Modifications in these regions of the DNA may lower the pathogenicity of the virus, i.e., attenuate the virus. For example, inactivation of the thymidine kinase gene renders human herpes simplex virus non-pathogenic (13), and pseudorabies virus of swine non-pathogenic (14).

Removal of part of the repeat region renders human herpes simplex virus non-pathogenic (16,17). A repeat region has been identified in Marek's disease virus that is associated with viral oncogenicity (18). A region in herpesvirus saimiri has similarly been correlated with oncogenicity (19). Removal of part of the repeat region renders pseudorabies virus non-pathogenic (U.S. Pat. No. 4,877,737, issued Oct. 31, 1989). A region in pseudorabies virus has been shown to be deleted in naturally-occurring vaccine strains (7,15) and it has been shown that these deletions are at least partly responsible for the lack of pathogenicity of these strains.

It is generally agreed that herpesviruses contain non-essential regions of DNA in various parts of the genome, and that modifications of these regions can attenuate the virus, leading to a non-pathogenic strain from which a vaccine may be derived. The degree of attenuation of the virus is important to the utility of the virus as a vaccine. Deletions which cause too much attenuation of the virus will result in a vaccine that fails to elicit an adequate immune response. Although several examples of attenuating deletions are known, the appropriate combination of deletions is not readily apparent.

The natural host of pseudorabies virus is swine, in which infection is commonly not apparent but may be characterized by fever, convulsions and paralysis. Pseudorabies virus also infects cattle, sheep, dogs, cats, foxes and mink, where infection usually results in death of the host. The predominant visible feature of pseudorabies viral infection is intense pruritus generally resulting in host mutilation of the involved area. Violent excitement, fits and paralysis, all symptoms of encephalomyelitis, precede death which usually occurs within a few days following onset of clinical signs.

Pseudorabies virus disease in swine is of serious concern to governmental bodies worldwide. In the United States, swine from infected herds cannot be sold except to slaughterhouses. The U.S. Department of Agriculture has enacted an eradication program to eliminate pseudorabies. Prior to the development of specific differential vaccines and companion diagnostic tests, any animal vaccinated for pseudorabies was treated as though it were infected and was subjected to the same regulatory constraints. With the advent of differential vaccines, regulations have been modified to allow interstate shipment of vaccinated, non-infected swine provided the differential vaccine/diagnostic test combination has been approved for use in the Cooperative State-Federal Pseudorabies Eradication Program (Federal Register, Vol. 55, No. 90, pp. 19245-19253 (May 9, 1990)).

The construction of differential vaccines has focused on the deletion of one of the glycoproteins of PRV. Theoretically, the glycoprotein chosen to be the diagnostic marker should have the following characteristics: (1) the glycoprotein and its gene should be non-essential for the production of infectious virus; (2) the glycoprotein should elicit a strong and persistent response in the animal; (3) the glycoprotein should not make a contribution to the protective immune response. Three glycoproteins gD, gH, and gB(II) (25) fail the first criteria. Each has a counterpart in herpes simplex virus (HSV) which has proven to be essential (20). g63 is a minor glycoprotein and would not be expected to elicit a major serological response (8). gIII has been shown to make a significant contribution to protective immunity as a target of neutralizing antibodies (10) and as a target of cell-mediated immunity (21). gI is also the target of neutralizing antibodies (22) and might be expected to play a role in protective immunity. Only gpX meets all three of the theoretical criteria (25).

Currently, there are five USDA-licensed, modified live, differential PRV vaccines available. They are PRV/MARKER ® (SyntroVet Incorporated), TOLVID ® (Upjohn), PRV vaccine (Boehringer Ingelheim), PRVAC® (SmithKline Beecham Animal Health) and OMNIMARK ™ (Fermenta Animal Health). The companion diagnostic test for each of these vaccines is directed against one of three PRY glycoproteins (gpX, gI or gIII). In each case, the gene coding for the diagnostic glycoprotein has either been altered by genetic engineering or has been shown to be deleted in a naturally occurring virus. The diagnostic marker deleted from PRY/Marker and Tolvid is gpX, which was altered by genetic engineering techniques. PRV vaccine and PRVac contain viruses that have a spontaneous deletion of gI from a naturally occurring virus. gIII is deleted from OmniMark, as a result of genetic engineering.

As the pseudorabies eradication program progresses, it would be of great value to have a confirmatory diagnostic test. Due to differing antigenicity of each diagnostic antigen and to the nature of the immune response of individual animals, the level of antibody to the diagnostic antigen can vary widely. A vaccine which incorporates a second diagnostic marker which could be used in a confirmatory test would be of great value. Two virus strains have been described which have incorporated the deletion of two glycoproteins for the purposes of serologic differentiation. One of these, described by Kit et al. (U.S. Pat. No. 4,711,850), has a genetically engineered deletion of gIII and a naturally occurring deletion of gI. As discussed above, both of these glycoproteins are targets of neutralizing antibody and gIII is also the target of cell-mediated immunity. The deletion of both of these important antigens would be expected to compromise the efficacy of a vaccine. The second virus, described by Post et al. (25) has been genetically engineered to incorporate deletions in both the gpX and gI genes. The authors concluded that this virus was significantly compromised in efficacy relative to a virus in which only the gpX was deleted. In summary, the current state of the art indicates that a virus deleted in both gpX and gI would not be effective as a vaccine.

A vaccine superior to the currently available products would have the following characteristics: (1) not produce clinical signs in 3–4 day old piglets; (2) give 95% protection in pigs of all ages; (3) permit serological differentiation from wild-type infected animals: and (4) permit a confirmatory diagnostic test. This invention provides such a superior vaccine, unexpectedly, by deleting specific regions of both gpX and gI.

SUMMARY OF THE INVENTION

Specifically, the present invention provides an attenuated, genetically-engineered pseudorabies virus designated S-PRV-155 (ATCC Accession No. VR 2311). The present invention also provides a vaccine which comprises an effective immunizing amount of the attenuated, genetically-engineered pseudorabies virus designated S-PRV-155 and a suitable carrier. The invention further provides a method of immunizing an animal against disease caused by pseudorabies virus which comprises administering to the animal an effective immunizing dose of the vaccine of the present invention. Finally, the invention provides a method for distinguishing an animal vaccinated with the vaccine of the present invention from an animal infected with a naturally-occurring, wild-type pseudorabies virus.

The following abbreviations are used: protein kinase (PK), glycoprotein X (gpX), glycoprotein 50 (g50), glycoprotein 63 (g63), pseudorabies virus (PRV), and polyadenylation signal (pA).

Figure 1:
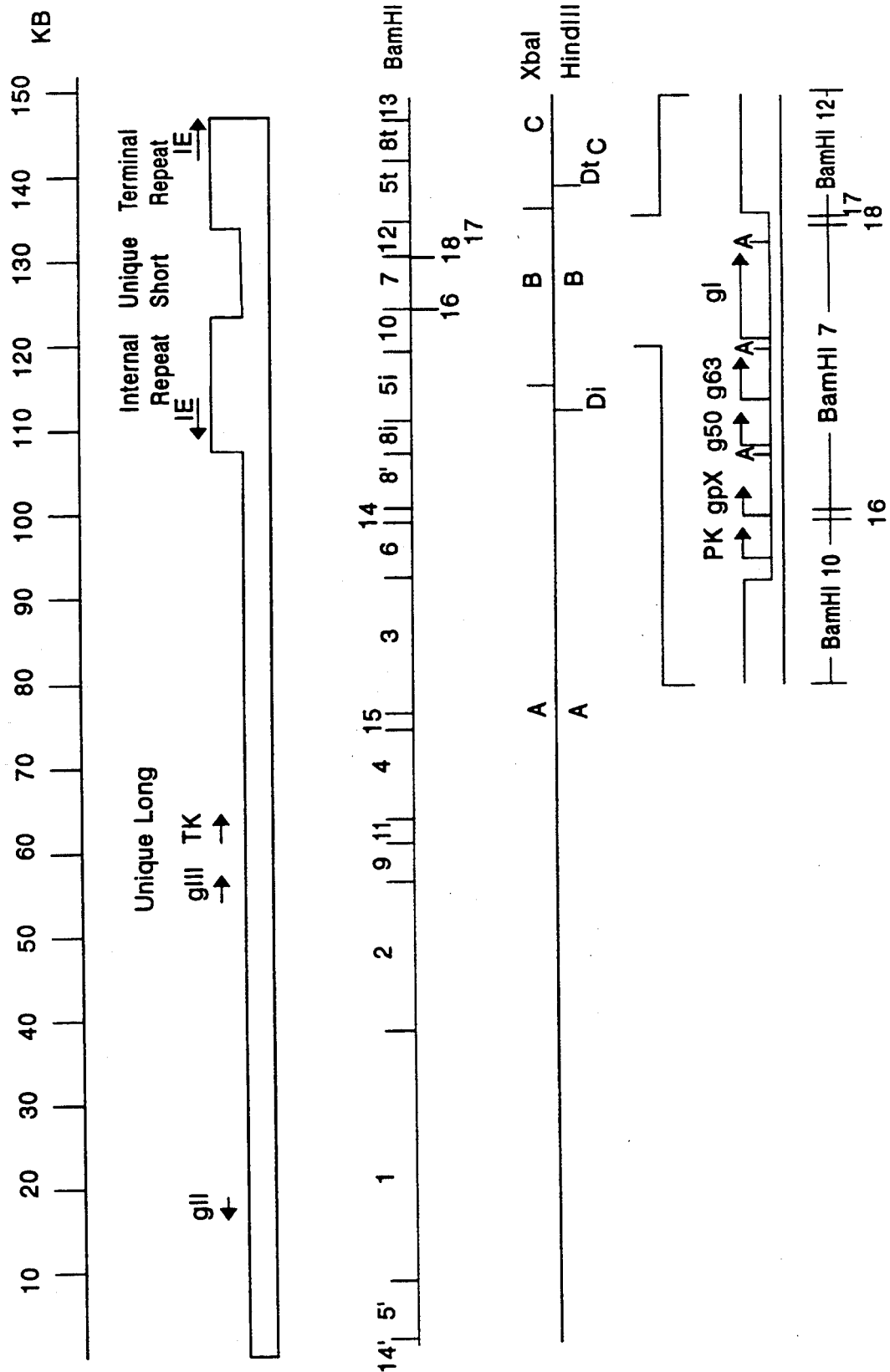
FIG. 1. Details of the PRV Strain ISU S62/26. Diagram of PRV genomic DNA showing the unique long, internal repeat, unique short, and terminal repeat regions. Restriction maps for the enzymes BamHI, XbaI, and HindIII are indicated. Fragments are numbered or lettered in order of decreasing size. The unique short region is also expanded for inclusion of more detail. The location of several genes is also indicated; they are glycoprotein II (gII) (24), glycoprotein III (gIII) (23), thymidine kinase (TK), immediate early gene (IE), protein kinase (PK) (3), glycoprotein X (gpX) (4), glycoprotein 50 (g50) (5), glycoprotein 63 (g63) (6), and glycoprotein I (gI) (6).
Figure 2A:
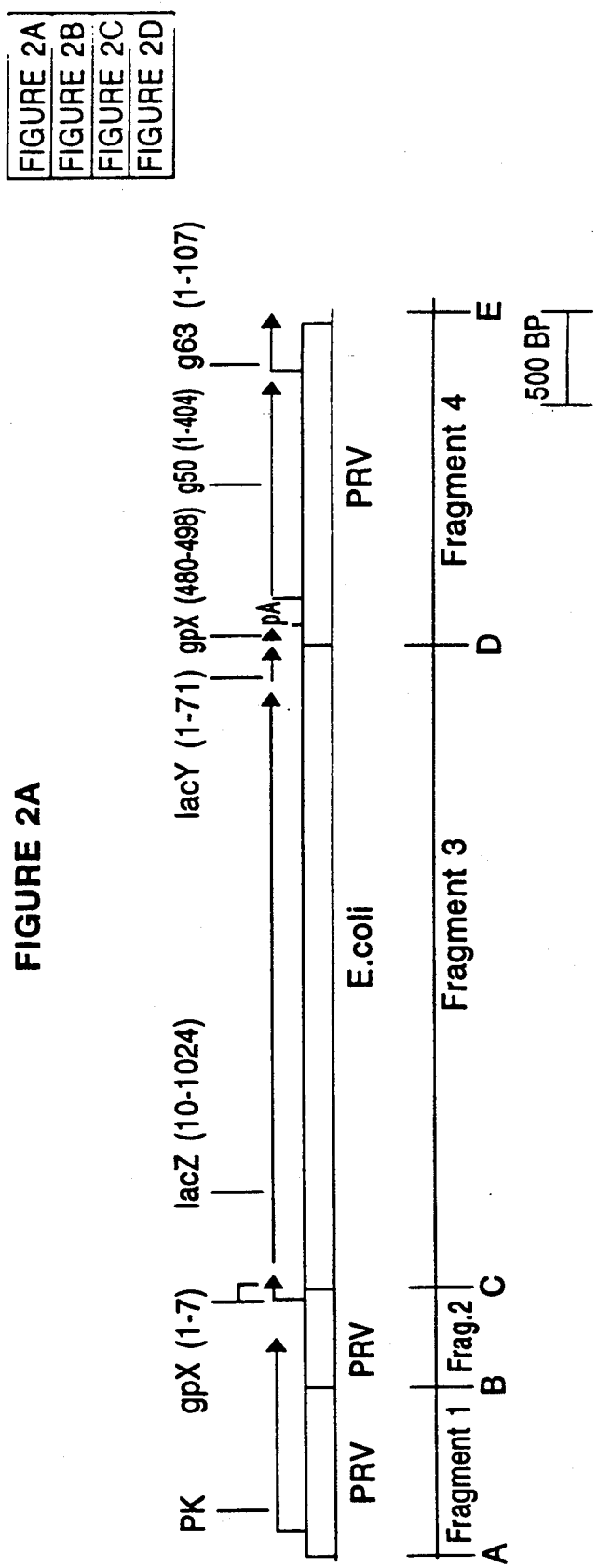
FIGS. 2A–2D. Detailed description of the DNA insertion in Homology Vector 263-58.18. Diagram showing the orientation of DNA fragments assembled in plasmid 263-58.18. The origin of each fragment is indicated in the table. The sequences located at each of the junctions between fragments is also shown. The restriction sites used to generate each fragment as well as synthetic linker sequences which were used to Join the fragments are described for each Junction. The synthetic linker sequences are underlined by a heavy bar. The location of several gene coding regions and regulatory elements is also given. The following conventions are used: numbers in parentheses, (), refer to amino acids relative to the references given in FIG. 1, and restriction sites in brackets, [], indicate the remnants of sites which were destroyed during construction.
Figure 2B:
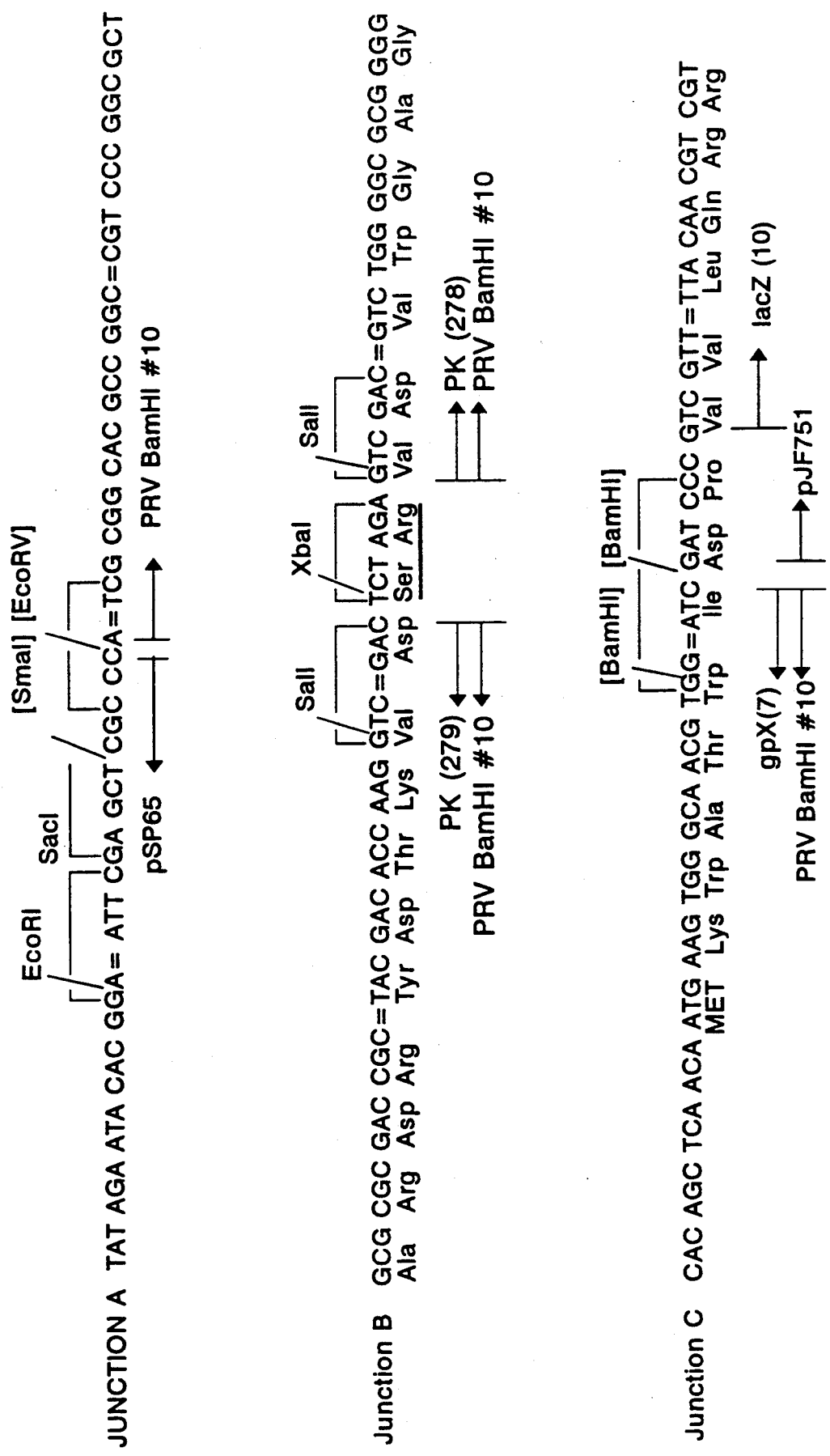
Figure 2C:
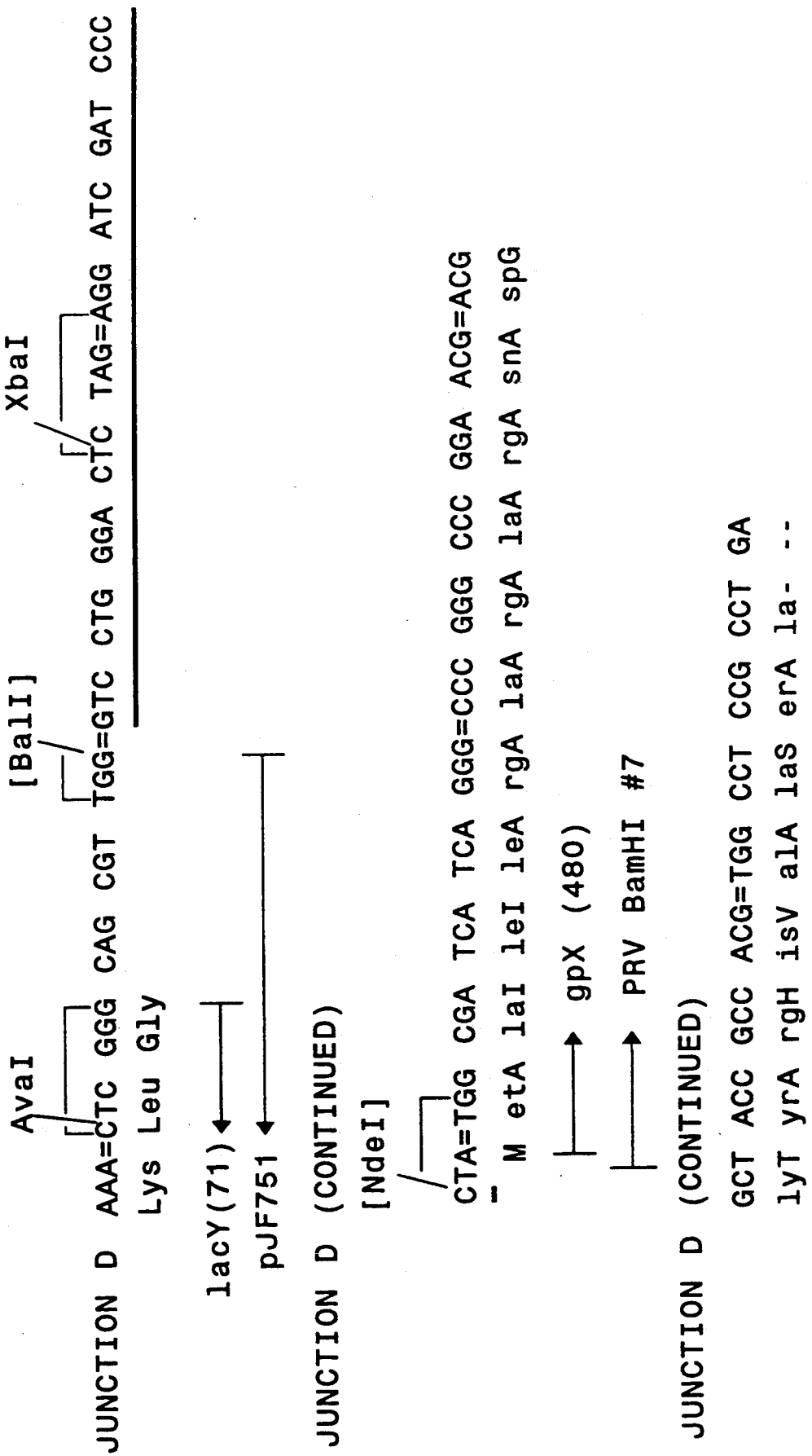
Figure 2D:
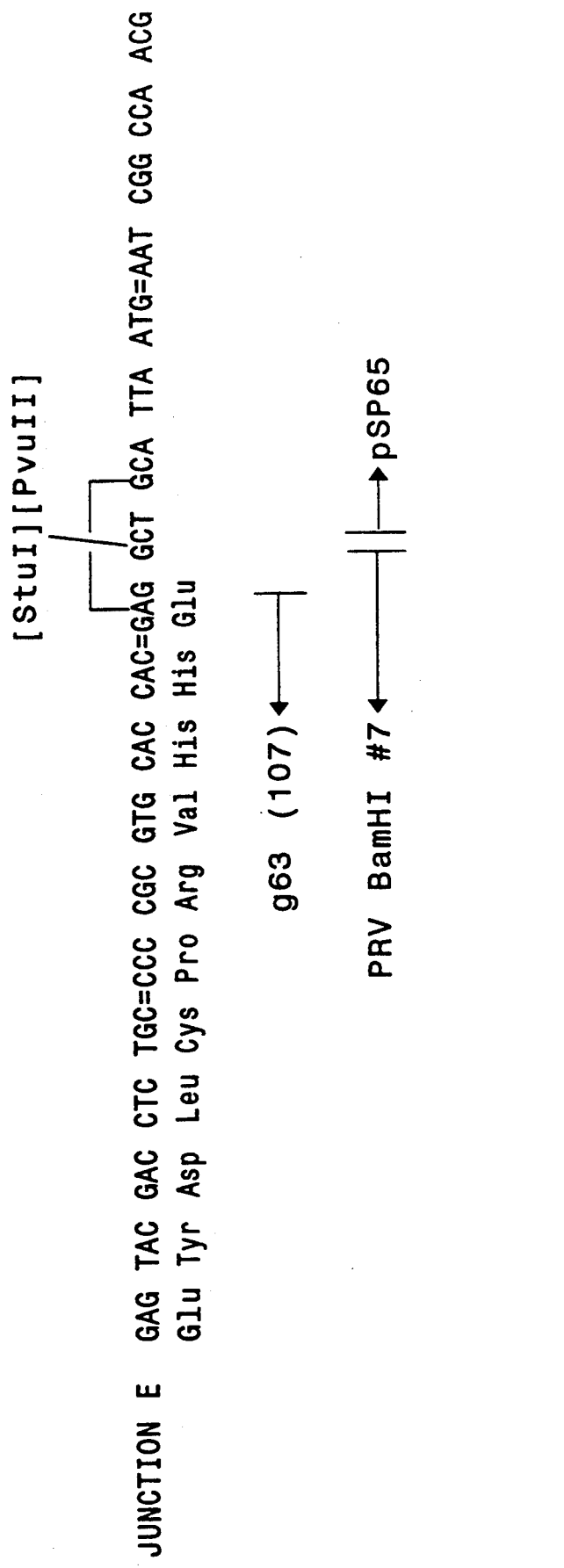
Figure 3B:
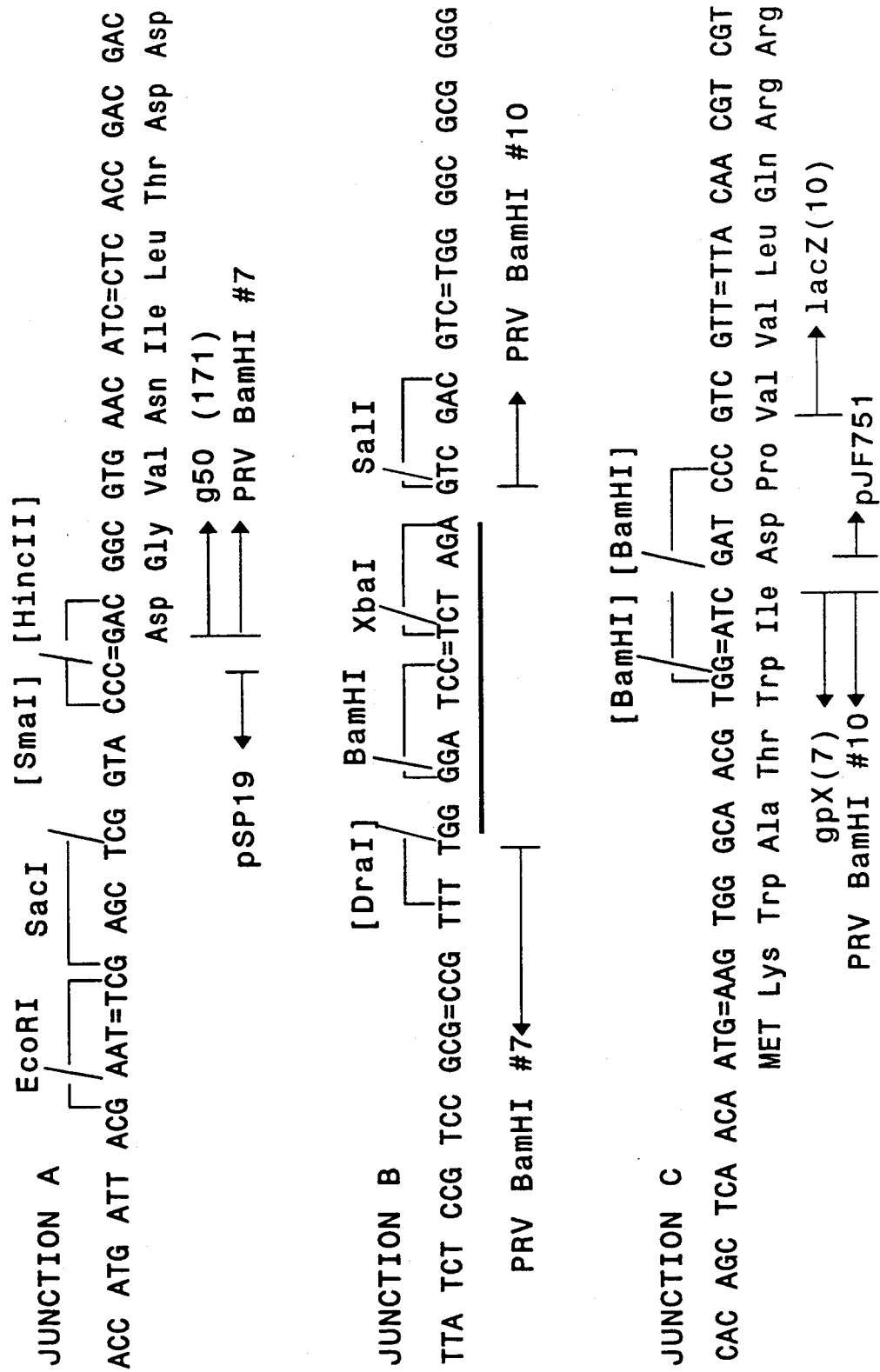
Figure 3D:
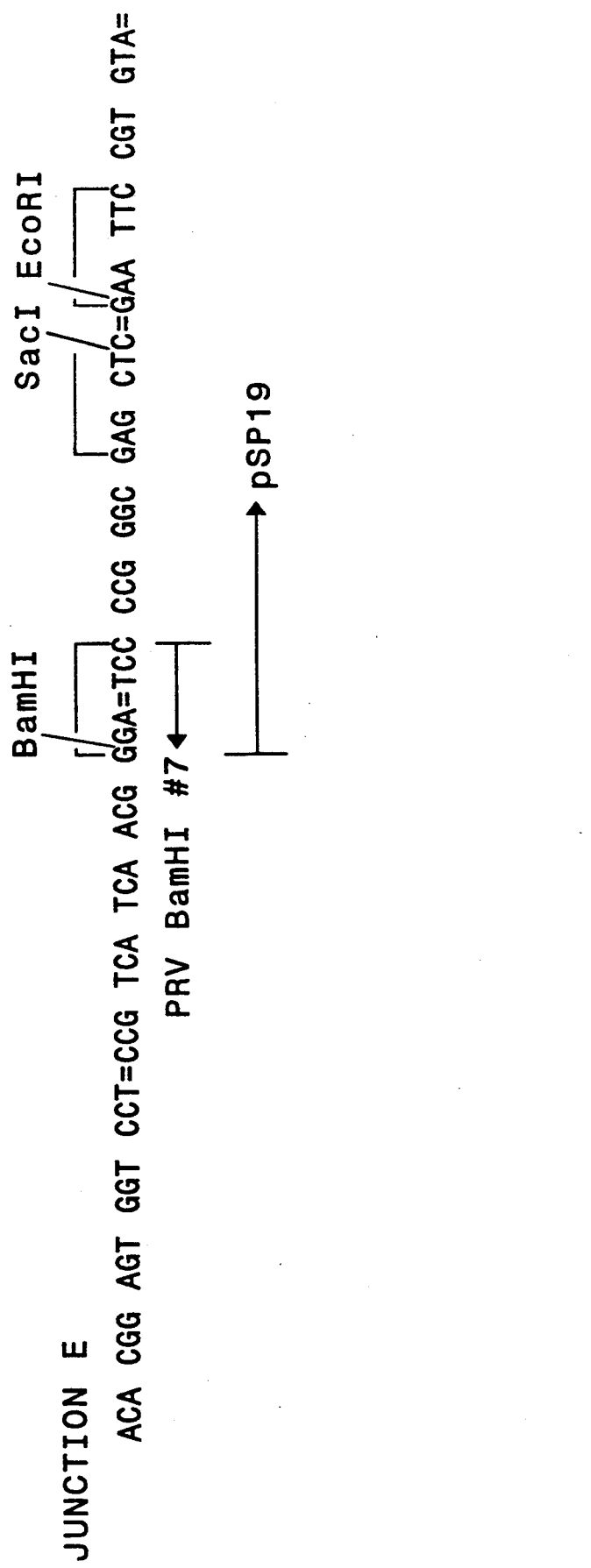
Figure 4D:
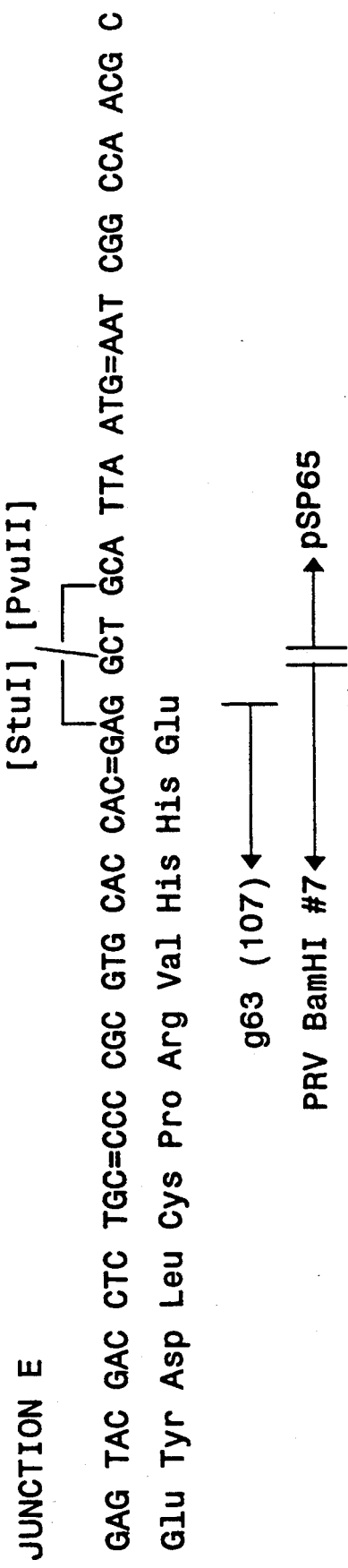

FIGS. 3A–3D. Detailed description of the DNA insertion in Homology Vector 416-09.2H. Diagram showing the orientation of DNA fragments assembled in plasmid 416-09.2H. The origin of each fragment is indicated in the table. The sequences located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following conventions are used: numbers in parentheses, (), refer to amino acids relative to the references given in FIG. 1, and restriction sites in brackets, [], indicate the remnants of sites which were destroyed during construction. The following abbreviations are used: protein kinase (PK), glycoprotein X (gpX), glycoprotein 50 (g50), glycoprotein 63 (g63), pseudorabies virus (PRV), and polyadenylation signal (pA).

FIGS. 4A–4D. Detailed description of the DNA insertion in Homology Vector 436-86.32K. Diagram showing the orientation of DNA fragments assembled in plasmid 436-86.32K. The origin of each fragment is indicated in the table. The sequences located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following conventions are used: numbers in parentheses, (), refer to amino acids relative to the references given in FIG. 1, and restriction sites in brackets, [], indicate the remnants of sites which were destroyed during construction. The following abbreviations are used: protein kinase (PK), glycoprotein X (gpX), glycoprotein 50 (g50), glycoprotein I (gI), pseudorabies virus (PRV), human cytomegalovirus (HCMV), and polyadenylation signal (pA).

DETAILED DESCRIPTION OF THE INVENTION

The present invention provides an attenuated, genetically-engineered pseudorabies virus designated S-PRV-155 (ATCC Accession No. VR 2311). The S-PRV-155 pseudorabies virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2311. The present invention also provides a vaccine which comprises an effective immunizing amount of the attenuated, genetically-engineered pseudorabies virus designated S-PRV-155 and a suitable carrier. The vaccine may contain either inactivated or live pseudorabies virus S-PRV-155.

Suitable carriers for the pseudorabies virus are well known in the art and include proteins, sugars, etc. One example of such a suitable carrier is a physiologically balanced culture medium containing one or more stabilizing agents such as stabilized, hydrolyzed proteins, lactose, etc.

In general, the vaccine of this invention contains an effective immunizing amount of S-PRV-155 virus of from about $10^3$ to $10^9$ PFU/dose. Preferably, the effective immunizing amount is from about $10^4$ to $10^6$ PFU/dose for the live vaccine and from about $10^7$ to $10^9$ PFU/dose for the inactivated vaccine. Preferably, the live vaccine is created by taking tissue culture fluids and adding stabilizing agents such as stabilized, hydrolyzed proteins. Preferably, the inactivated vaccine uses tissue culture fluids directly after inactivation of the virus.

The present invention also provides a method of immunizing an animal, particularly a swine, against disease caused by pseudorabies virus which comprises administering to the animal an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

The present invention also provides a method for distinguishing an animal vaccinated with the vaccine of the present invention from an animal infected with a naturally-occurring, wild-type pseudorabies virus. This method comprises analyzing a sample of a body fluid from the animal for the presence of gpX and at least one other antigen normally expressed in an animal infected by a naturally-occurring, wild-type pseudorabies virus and determining whether the antigen and gpX are present in the body fluid. The presence of the antigen and the absence of gpX in the body fluid is indicative of an animal vaccinated with the vaccine and not infected with a naturally-occurring, wild-type pseudorabies virus. The presence of the antigen and of gpX in the body fluid may be determined by various methods, for example, by detecting in the body fluid antibodies specific for the antigen and for gpX. The method for distinguishing an animal vaccinated with the vaccine of the present invention from an animal infected with a naturally-occurring, wild-type pseudorabies virus may further comprise analyzing the sample for the presence of gI. The presence of the antigen and the absence of gI in the body fluid is indicative of an animal vaccinated with the vaccine and not infected with a naturally-occurring, wild-type pseudorabies virus. Within this application, a naturally-occurring pseudorabies virus means a pseudorabies virus which has not been genetically engineered, and includes, but is not limited to, wild-type pseudorabies viruses and pseudorabies viruses selected from pseudorabies viruses which exist in nature and have spontaneous deletions. Within this application, nonessential gene means a gene which is not essential for viral replication.

The present invention also provides a further method for distinguishing an animal vaccinated with the vaccine of the present invention from an animal infected with a naturally-occurring, wild-type pseudorabies virus. This method comprises analyzing a sample of a body fluid from the animal for the presence of gI and at least one other antigen normally expressed in an animal infected by a naturally-occurring, wild-type pseudorabies virus and determining whether the antigen and gI are present in the body fluid. The presence of the antigen and the absence of gI in the body fluid is indicative of an animal vaccinated with the vaccine and not infected with a naturally-occurring, wild-type pseudorabies virus.

Methods for constructing, selecting and purifying pseudorabies viruses, including S-PRV-155, are detailed in the Materials and Methods section which follows.

MATERIALS AND METHODS

PREPARATION OF PSEUDORABIES VIRUS (PRV) STOCK SAMPLES. Pseudorabies virus (PRV) stock samples were prepared by infecting Vero cells at a multiplicity of infection of 0.01 plaque forming units (PFU)/cell in Dulbecco's Modified Eagle (DME) medium containing 2 mM glutamine, 100 units/ml penicillin and 100 units/ml streptomycin (these components were obtained from Irvine Scientific or an equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. The cells were resuspended in 1/10 the original volume of medium and an equal volume of two times autoclaved skim milk (9% skim milk powder in $H_2O$ wgt/vol) was added. The virus sample was frozen and thawed two times, aliquoted and stored frozen at $-70°$ C. The titer was usually about $10^8$ PFU/ml.

TITRATION OF PRV. For PRV titrations, Vero cells were plated in 60 mm petri dishes at $5 \times 10^5$ cells/mi. The next day growth medium (complete DME plus 10% fetal bovine serum) was replaced with 3.0 ml/dish of maintenance medium (complete DME plus 1% fetal bovine serum). Virus stocks were diluted 1:$10^4$, $10^5$, $10^6$, $10^7$, and $10^8$ in maintenance medium. From these dilutions, 1.0 ml was added to each dish. Dishes were set at 37° C. in a humidified incubator with 5% $CO_2$ for 4 hours. The media was then aspirated and each dish was overlaid with 5.0 ml 0.75% final concentration of low melting point agarose in 2X Minimal Essential Media (MEM) containing 2 mM glutamine, 100 units/ml penicillin, 100 units/ml streptomycin, and 2% fetal bovine serum. Dishes were set at room remperature for 30 minutes, to let the agarose set, and then placed at 37° C. in a humidified incubator with 5% $CO_2$ for 3 days. Plaques were counted and PFU/ml calculated.

PREPARATION OF PRV DNA. For PRV DNA preparation a confluent monolayer of Vero cells in a 25 $cm^2$ flask or a 60 mm petri dish was infected with 100 microliters of virus sample in 1 ml medium. Adsorption proceeded for 1-2 hours at 37° C. in a humidified incubator with 5% $CO_2$ in air. After adsorption, 4 mls of complete DME medium plus 1% fetal bovine serum were added. After overnight incubation, or when the cells were showing 100% cytopathic effect, the cells were scraped into the medium with a cell scraper (Costar brand). The cells and medium were centrifuged at 3000 rpm for 5 minutes in a clinical centrifuge. The medium was decanted and the cell pellet was gently resuspended in a 0.5 ml solution containing 0.01M Tris pH 7.5, 1 mM EDTA and 0.5% Nonidet P-40 (NP40). The sample was incubated at room temperature for 10 minutes. Ten microliters of a stock solution of RNase A (Sigma) were added (stock is 10 mg/ml, boiled for 10 minutes to inactivate DNase). The sample was centrifuged for 5 minutes at 3000 rpm in a clinical centrifuge to pellet nuclei. The DNA pellet was removed with a pasteur pipette or wooden stick and discarded. The supernatant fluid was decanted into a 1.5 ml Eppendorf tube containing 25 microliters of 20% sodium dodecyl sulfate (Sigma) and 25 microliters proteinase-K (10 mg/ml; Boehringer Mannhiem). The sample was mixed and incubated at 37° C. for 30-60 minutes. An equal volume of water-saturated phenol was added and the sample was mixed on a vortex mixer. The sample was centrifuged in an Eppendorf minifuge for 5 minutes at full speed. The upper aqueous phase was removed to a new Eppendorf tube, two volumes of −20° C. absolute ethanol were added and the tube was put at −20° C. for 30 minutes to precipitate nucleic acid. The sample was centrifuged in an Eppendorf centrifuge at 4° C. for 5 minutes. The supernatant was decanted and the pellet was washed one time with cold 80% ethanol. The pellet was rehydrated in 17 microliters of water. For the preparation of larger amounts of DNA, the procedure was scaled up to start with an 850 $cm^2$ roller bottle of Vero cells. The DNA was stored in water or 0.01M Tris pH 7.5, 1 mM EDTA at 4° C.

PHENOL EXTRACTION. Phenol extraction was performed on any convenient volume of DNA sample, typically between 100 microliters to 1 ml. The DNA sample was diluted in 0.01M Tris pH 7.5, 1 mM EDTA and an equal volume of water saturated phenol was added. The sample was mixed briefly on a vortex mixer and placed on ice for 3 minutes. After centrifugation for 3 minutes in a microfuge, the aqueous layer was removed to a new tube and was precipitated by ethanol.

ETHANOL PRECIPITATION. DNA in a sample was concentrated by ethanol precipitation. To the DNA sample was added 1/10 volume of 3M sodium acetate, pH 7.5 and 3 volumes of cold ethanol. The DNA was precipitated for 30 minutes at −70° C. or overnight at −20° C. and then pelleted by centrifugation in the microfuge for 15 minutes at 4° C. The pellet was washed once with 200 microliters of cold 80% ethanol and pelleted again for 10 minutes at 4° C. After air drying or lyophilization, the pellets were resuspended in the appropriate buffer or water.

RESTRICTION ENZYME DIGESTION. DNA was cut by restriction enzymes using the buffer recommended by the manufacturer (IBI, BRL, New England Biolabs, etc). Whenever possibile, the concentration of DNA was kept below 1 microgram/50 microliters. Incubation was at 37° C. for 1-4 hours.

AGAROSE GEL ELECTROPHORESIS OF DNA. To visualize the restriction pattern of the DNA, 5 microliters of loading buffer (5X electrophoresis buffer, 0.01% bromphenol blue dye, 50 mM EDTA, and 50% glycerol) were added. The sample was loaded into a lane in a horizontal submarine electrophoresis unit containing a 0.6% to 3.0% agarose gel. The electrophoresis buffer was 40 mM Tris, 10 mM EDTA, adjusted to pH 7.8 with acetic acid, and with or without 0.5 micrograms/ml ethidium bromide. The gel was run at 40-50 volts for 18 hours, removed and stained with 0.5 micrograms/ml ethidium bromide for 30 minutes, and the DNA bands were visualized on a long wavelength UV transilluminator.

LIGATION. DNA was joined together by the action of the enzyme T4 DNA ligase (BRL). Ligation reactions contained various amounts of DNA (from 0.2 to 20 µg), 20 mM Tris pH 7.5, 10 mM $MgCl_2$, 10 mM dithiothreitol (DTT), 200 µM ATP and 20 units T4 DNA ligase in 10-20 µl final reaction volume. The ligation proceeded for 3-16 hours at 15° C.

SOUTHERN BLOTTING OF DNA. Southern blots utilized the Nonradioactive DNA Labeling and Detection Kit of Boehringer Mannheim. The manufacturer's recommended procedures were followed.

DNA TRANSFECTION FOR GENERATING RECOMBINANT VIRUS. The method is based upon the calcium phosphate procedure of Graham and Van der eb (1) with the following modifications. Virus and/or Plasmid DNA were diluted to 298 µl in 0.01M Tris pH 7.5, 1 mM EDTA. Forty µl 2M $CaCl_2$ was added followed by an equal volume of 2X HEPES buffered saline (10 g N-2-hydroxyethyl piperazine N'-2-ethanesulfonic acid (HEPES), 16 g NaCl, 0.74 g KCl, 0.25 g $Na_2HPO_4.2H_2O$, 2 g dextrose per liter $H_2O$ and buffered with NaOH to pH 7.4). The mixture was then incubated on ice for 10 minutes, and then added dropwise to an 80% confluent monolayer of Veto cells growing in a 60 mm petri dish under 5 ml of medium (DME plus 2% fetal bovine serum). The cells were incubated four hours at 37° C. in a humidified incubator containing 5% $CO_2$. The cells were then washed with three 5 ml aliquots of 1XPBS (1.15 g $Na_2HPO_4$, 0.2 g $KH_2PO_4$, 0.8 g NaCl, 0.2 g KCl per liter $H_2O$), and fed with 5 ml of medium (DME plus 2% fetal bovine serum). The cells were incubated at 37° C. as above for 3-7 days until cytopathic effect from the virus was 50-100%. Virus was harvested as described above for the preparation of virus stocks. This stock is referred to as a transfection stock and was subsequently screened for recombinant virus by the BLUOGAL SCREEN FOR RECOMBINANT PRV.

HOMOLOGOUS RECOMBINATION PROCEDURE FOR GENERATING RECOMBINANT PRV. This method relies upon the homologous recombination between PRV DNA and plasmid homology vector DNA which occurs in Vero cells co-transfected with these elements. From 0.1.-1.0 µg of plasmid DNA containing foreign DNA flanked by appropriate PRV cloned sequences (the homology vector) were mixed with approximately 0.3 µg of intact PRV DNA. The DNA are diluted to 298 µl in 0.01M Tris pH 7.5, 1 mM EDTA and transfected into Vero cells according to the DNA TRANSFECTION FOR GENERATING RECOMBINANT VIRUS (see above).

DIRECT LIGATION PROCEDURE FOR GENERATING RECOMBINANT PRV. Rather than using homology vectors and relying upon homologous recombination to generate recombinant virus, we have also developed the technique of direct ligation to engineer PRY. In this instance, a cloned foreign gene did not require flanking PRY DNA sequences but only required that it have restriction sites available to cut out the foreign gene fragment from the plasmid vector. A compatible restriction enzyme was used to cut PRV DNA. A requirement of the technique was that the restriction enzyme used to cut the PRV DNA must cut at a limited number of sites, at least one of the sites being a nonessential site. We have used XbaI, which cuts PRV DNA in two places. We have also used HindIII which cuts PRV DNA in four places. Restriction sites previously introduced into PRV by other methods may also be used. The PRV DNA was mixed with a 30-fold molar excess of plasmid DNA (typically 5 μg of virus DNA to 10 μg of plasmid DNA), and the mixture was cut with the appropriate restriction enzyme. The DNA mixture was phenol extracted and ethanol precipitated to remove restriction enzymes, and ligated together according to the ligation procedure detailed above. The ligated DNA mixture was then resuspended in 298 μl 0.01M Tris pH 7.5, 1 mM EDTA and transfected into Vero cells according to the DNA TRANSFECTION FOR GENERATING RECOMBINANT VIRUS (see above).

The direct ligation procedure may also be used to delete DNA from PRY. Non-essential DNA which is flanked by appropriate restriction enzyme sites may be deleted by digesting the PRV with such enzymes and religation. The frequency of engineered viruses generated by the direct ligation procedure is high enough that screening can be accomplished by restriction enzyme analysis of randomly picked plaques from the transfection stock.

BLUOGAL SCREEN FOR RECOMBINANT PRV. When the E. coli β-galactosidase marker gene was incorporated into a recombinant virus the plaques containing recombinants were visualized by a simple assay. The chemical BLUOGAL™ (halogenated indolyl-B-D-galactoside)(Bethesda Research Labs) was incorporated (200 μg/ml) into the agarose overlay during the plaque assay, and plaques that expressed active β-galactosidase turned blue. The blue plaques were then picked onto fresh Vero cells and purified by further blue plaque isolations. In recombinant virus strategies in which the E. coli β-galactosidase marker gene is removed the assay involves plaque purifying white plaques from a background of parental blue plaques. In both cases viruses were typically purified with three rounds of plaque purification.

CONSTRUCTION OF DELETION VIRUSES. The strategy used to construct deletion viruses involved the use of both homologous recombination and direct ligation techniques. Initially, a virus was constructed via homologous recombination in which the gene to be deleted was replaced with the E. coli β-galactosidase marker gene. A second virus was then constructed via direct ligation in which the marker gene was deleted. This strategy requires that the marker gene introduced into the first virus must be flanked by appropriate restriction enzyme sites as described in the DIRECT LIGATION PROCEDURE FOR GENERATING RECOMBINANT PRV. The advantage of this strategy is that both viruses may be purified by the BLUOGAL SCREEN FOR RECOMBINANT PRV. The first virus is purified by picking blue plaques from a white background, the second virus is purified by picking white plaques from a blue plaque background. Three different homology vectors were constructed for the purpose of deleting the gpX and gpI gene coding regions. A detailed description of these homology vectors follows.

HOMOLOGY VECTOR 263-58.18. The plasmid 263-58.18 was constructed for the purpose of deleting the gpX gene coding region from the pseudorabies virus. It incorporates an E. coli β-galactosidase marker gene flanked by PRV DNA. Upstream of the marker gene is an approximately 1330 base pair fragment of PRV DNA which ends with sequences encoding the first seven amino acids (4) of the gpX primary translation product. Downstream of the marker gene is an approximately 1800 base pair fragment of PRV DNA which begins with sequences encoding the last 19 amino acids (4) of the gpX primary translation product. When this plasmid is used according to the HOMOLOGOUS RECOMBINATION PROCEDURE FOR GENERATING RECOMBINANT PRV it will replace the DNA coding for amino acids 8-479 of the gpX primary translation product with DNA coding for the marker gene. Note that the β-galactosidase (lacZ) marker gene will be under the control of the endogenous gpX promoter. A detailed description of the plasmid is given in FIGS. 2A-2D. It was constructed from the indicated DNA sources utilizing standard recombinant DNA techniques (2). It may be constructed by joining restriction fragments from the following sources with the synthetic DNA sequences indicated in FIGS. 2A-2D. The plasmid vector is derived from an approximately 2792 base pair SmaI to PvuII restriction fragment of pSP65 (Promega). Fragment 1 is an approximately 922 base pair EcoRV to SalI restriction fragment of the PRY BamHI restriction fragment #10 (15). Fragment 2 is an approximately 412 base pair SalI to BamHI restriction fragment of the PRV BamHI restriction fragment #10 (15). Fragment 3 is an approximately 3347 base pair BamHI to BalI restriction fragment of plasmid pJF751 (11). Fragment 4 is an approximately 1803 base pair NdeI to StuI restriction fragment from the PRV BamHI restriction fragment #7 (15). Note that the XbaI sites located at Junction B and Junction D are the only XbaI sites in this plasmid and permit the marker gene to be cut out as an XbaI restriction fragment.

HOMOLOGY VECTOR 416-09.2H. The plasmid 416-09.2H was constructed for the purpose of deleting the gI gene coding region from the pseudorabies virus. It incorporates an E. coli β-galactosidase marker gene flanked by PRV DNA. Upstream of the marker gene is an approximately 1884 base pair fragment of PRV DNA which ends with sequences located approximately 46 base pairs upstream of the first amino acid (6) of the gI primary translation product. Downstream of the marker gene is an approximately 1309 base pair fragment of PRV DNA which begins with sequences encoding the last 105 amino acids (6) of the gI primary translation product. When this plasmid is used according to the HOMOLOGOUS RECOMBINATION PROCEDURE FOR GENERATING RECOMBINANT PRV, it will replace the DNA coding for amino acids 1-472 of the gI primary translation product with DNA coding for the marker gene. Note that the β-galactosidase (lacZ) marker gene will be under the control of the gpX promoter. A detailed description of the plasmid is given in FIGS. 3A-3D. It was constructed from the indicated DNA sources utilizing standard recombinant DNA techniques (2). It may be constructed by joining restriction fragments from the following sources with the synthethic DNA sequences indicated in FIGS. 3A-3D. The plasmid vector is derived from an approximately 3009 base pair SmaI to BamHI restriction fragment of pSP19 (Promega). Fragment 1 is an approximately 1884 base pair HincII to DraI restriction fragment of the PRV BamHI restriction fragment #7 (15). Fragment 2 is an approximately 412 base pair SalI to BamHI restriction fragment of the PRV BamHI restriction fragment #10 (15). Fragment 3 is an approximately 3347 base pair BamHI to BalI restriction fragment of plasmid pJF751 (11). Fragment 4 is an approximately 1309 base pair SphI to BamHI restriction fragment from the PRV BamHI restriction fragment #7 (15). Note that the XbaI sites located at Junction B and Junction D are the only XbaI sites in this plasmid and permit the marker gene to be cut out as an XbaI restriction fragment.

HOMOLOGY VECTOR 436-86.32K. The plasmid 436-86.32K was constructed for the purpose of deleting the gpX gene coding region from the pseudorabies virus. It incorporates an HCMV immediate early promoted E. coli β-galactosidase marker gene flanked by PRV DNA. Upstream of the marker gene is an approximately 1330 base pair fragment of PRV DNA which ends with sequences encoding the first seven amino acids (4) of the gpX primary translation product. Downstream of the marker gene is an approximately 1800 base pair fragment of PRV DNA which begins with sequences encoding the last 19 amino acids (4) of the gpX primary translation product. When this plasmid is used according to the HOMOLOGOUS RECOMBINATION PROCEDURE FOR GENERATING RECOMBINANT PRV, it will replace the DNA coding for amino acids 8-479 of the gpX primary translation product with DNA coding for the marker gene. A detailed description of the plasmid is given in FIGS. 4A–4D. It was constructed from the indicated DNA sources utilizing standard recombinant DNA techniques (2). It may be constructed by joining restriction fragments from the following sources with the synthetic DNA sequences indicated in FIG. 4. The plasmid vector is derived from an approximately 2792 base pair SmaI to PvuII restriction fragment of pSP65 (Promega). Fragment 1 is an approximately 1336 base pair EcoRV to BamHI restriction fragment of the PRV BamHI restriction fragment #10 (15). Fragment 2 is an approximately 1191 base pair PstI to AvaII restriction fragment of the HCMV XbaI restriction fragment E (12). Fragment 3 is an approximately 3002 base pair BamHI to PvuII restriction fragment of plasmid pJF751 (11). Note that this fragment contains two internal PvuII sites, requiring a partial PvuII digest. Alternatively, the fragment may be obtained as two fragments without the requirement of a partial digest. These two fragments are an approximately 2950 base pair BamHI to NdeI fragment and an approximately 55 base pair NdeI to PvuII fragment. These two fragments joined at the unique NdeI site may substitute for fragment 3. Fragment 4 is an approximately 1803 base pair NdeI to StuI restriction fragment from the PRY BamHI restriction fragment #7 (15). Note that the XbaI sites located at Junction B and Junction D are the only XbaI sites in this plasmid and permit the marker gene to be cut out as an XbaI restriction fragment.

VACCINATION STUDIES IN SWINE. Three-day-old pigs born to sows from swine herds free of pseudorabies were used to test the efficacy of the live, attenuated virus. The piglets were inoculated intramuscularly with 1 ml of virus fluid containing about $10^3$ to $10^5$ plaque forming units (PFU).

PRV-155 virus was also tested as an inactivated vaccine. The virus was inactivated by exposure to binary ethyleneimine for at least 40 hours at 37° C. Inactivated virus fluids were blended with an oil-based adjuvant and inoculated into four-week-old pigs.

Animals vaccinated with either live S-PRV-155 or with inactivated S-PRV-155 were observed each day after vaccination for adverse reactions (clinical signs of PRV disease). Samples of nasal secretions were obtained from pigs vaccinated with live S-PRV-155 and cultured to determine if the vaccine virus was capable of shedding and spreading to other animals. Immunity was determined by measuring PRV serum antibody levels and by challenging the vaccinated pigs with virulent virus at 3–4 weeks post-vaccination. In the latter case, the vaccinated animals and a group of non-vaccinated animals were inoculated with a virulent, pneumotropic strain of PRV (VDL4892), using an amount of challenge virus that caused PRY disease in at least 80% of the unvaccinated group of pigs. The challenged animals were observed daily for signs of disease and for nasal virus shedding. Serum samples were obtained at the time of challenge and at weekly intervals for 2–3 weeks post-vaccination. The serum was assayed for serum neutralizing (SN) antibody and for antibody to gpX (HERDCHEK ® (in vitro diagnostic test for detection of PRV gpX and gI antibodies, IDEXX corp.) and gpI with (HERDCHEK ® (in vitro diagnostic test for detection of PRV gpX and gI antibodies, IDEXX Corp.) and CLINEASE ® (in vitro diagnostic test for detection of PRV gI antibodies), SmithKline Beecham) according to manufacturer's recommendations.

EXAMPLES

Example 1

S-PRY-150

S-PRV-150 is a pseudorabies virus that has a deletion in the TK gene in the long unique region, a deletion in the repeat region, a 1460 base pair deletion in the gI coding region, and a 1825 base pair deletion in the gpX coding region. The gene for *E. coli* β-galactosidase (lacZ gene) was inserted in the place of the gPI gene and is under the control of the HCMV immediate early promoter.

S-PRV-150 was derived from S-PRV-002 (U.S. Pat. No. 4,877,737, issued Oct. 31, 1989) through the construction of three intermediate viruses. The first intermediate virus was S-PRV-070. In this virus the XbaI sites located in the repeat regions (see FIG. 1) were converted to EcoRI sites to allow for the use of XbaI restriction sites at other locations in subsequent steps. This was accomplished by inserting the synthetic oligonucleotide CTAGGAATTCC into the XbaI sites of S-PRV-002 utilizing the DIRECT LIGATION PROCEDURE FOR GENERATING RECOMBINANT PRV. In the second intermediate virus S-PRV-089, the gpX deletion was introduced along with the β-galactosidase marker gene. This was accomplished utilizing the homology vector 263-58.18 (see Materials and Methods) and virus S-PRV-070 in the HOMOLOGOUS RECOMBINATION PROCEDURE FOR GENERATING RECOMBINANT PRY. In the third intermediate virus (S-PRV-112) the β-galactosidase marker gene (lacZ) was removed by digestion with XbaI as described in the DIRECT LIGATION PROCEDURE FOR GENERATING RECOMBINANT PRV. Finally, S-PRV-150 was generated utilizing the homology vector 416-09.2H (see Materials and Methods) and virus S-PRV-153 in the HOMOLOGOUS RECOMBINATION PROCEDURE FOR GENERATING RECOMBINANT PRV. The structure of S-PRV-150 was confirmed by restriction enzyme analysis with BamHI and XbaI.

Example 2

S-PRV-151

S-PRV-151 is a pseudorabies virus that has a deletion in the TK gene in the long unique region, a deletion in the repeat region, a 1460 base pair deletion in the gI coding region, and a 1825 base pair deletion in the gpX coding region.

S-PRV-151 resulted from the removal of the marker gene from S-PRV-150 (see above). This was accomplished by digestion of S-PRY-150 with XbaI as described in the DIRECT LIGATION PROCEDURE FOR GENERATING RECOMBINANT PRV. The structure of S-PRV-151 was confirmed by restriction enzyme analysis with BamHI and XbaI.

The following experiment was conducted to determine if S-PRY-151 may be used as a vaccine to protect swine against pseudorabies disease. In this study, three-day-old piglets were vaccinated intramuscularly with S-PRV-151 as follows: 4 were inoculated with $10^6$ PFU and 4 were inoculated with $10^6$ PFU. A control group of 5 was also included in the study. The animals were observed, then challenged as described in VACCINATION STUDIES WITH SWINE (see Table I below).

TABLE I

VACCINATION OF 3-DAY-OLD PIGLETS WITH S-PRV-151 AND CHALLENGE WITH VIRULENT PRV

| | | SN Antibody[a] | | Post Challenge Observations | | |
|---|---|---|---|---|---|---|
| Virus Conc. | No. of pigs | Day 21 Post Vaccination | Day 14 Post Challenge | Virus Shedding[b] | Clinical Signs[c] | Death |
| $10^4$ PFU per Dose | 4 | ≦2 | 46 | 41% | 100% | 20% |
| $10^6$ PFU per Dose | 4 | ≦2 | 96 | 33% | 100% | 0 |
| None | 6 | <2 | 10 | 55% | 100% | 20% |

[a]Geometric mean titer (reciprocal of dilution)
[b]Percent of nasal secretion samples positive for virus
[c]Percent of pigs with CNS and/or respiratory manifestation In this experiment, all of the vaccinated animals remained healthy following vaccination, and did not shed vaccine virus in tonsillar secretions; however, neutralizing antibodies were not detected. After challenge with virulent virus, all vaccinates from both groups exhibited clinical signs of PRY disease. Although S-PRV-151 was shown to be safe in three-day-old piglets, this virus failed to demonstrate any protection in these animals.

Example 3

S-PRV-154

S-PRV-154 is a pseudorabies virus that has a deletion in the TK gene in the long unique region, a deletion in the repeat region, a 1460 base pair deletion in the gI coding region, and a 1414 base pair deletion in the gpX coding region. The gene for *E. coli* β-galactosidase (lacZ gene) was inserted in the place of the gpX gene and is under the control of the HCMV immediate early promoter.

S-PRV-154 was derived from S-PRV-002 (U.S. Pat. No. 4,877,737, issued Oct. 31, 1989) through the construction of three intermediate viruses. The first intermediate virus was S-PRV-070. In this virus, the XbaI sites located in the repeat regions (see FIG. 1) were converted to EcoRI sites to allow for the use of XbaI restriction sites at other locations in subsequent steps. This was accomplished by inserting the synthetic oligonucleotide CTAGGAATTCC into the XbaI sites of S-PRV-002 utilizing the DIRECT LIGATION PROCEDURE FOR GENERATING RECOMBINANT PRV. In the second intermediate virus S-PRV-146, the gI deletion was introduced along with the β-galactosidase marker gene. This was accomplished utilizing the homology vector 416-09.2H (see Materials and Methods) and virus S-PRV-070 in the HOMOLOGOUS RECOMBINATION PROCEDURE FOR GENERATING RECOMBINANT PRV. In the third intermediate virus (S-PRV-153) the β-galactosidase marker gene was removed by digestion with XbaI as described in the DIRECT LIGATION PROCEDURE FOR GENERATING RECOMBINANT PRV. Finally, S-PRV-154 was generated utilizing the homology vector 436 86.32K (see Materials and Methods) and virus S-PRV-153 in the HOMOLOGOUS RECOMBINATION PROCEDURE FOR GENERATING RECOMBINANT PRV. The structure of S-PRV-154 was confirmed by restriction enzyme analysis with BamHI and XbaI.

Example 4

S-PRV-155

S-PRV-155 is a pseudorabies virus that has a deletion in the TK gene in the long unique region, a deletion in the repeat region, a 1460 base pair deletion in the gI coding region, and a 1414 base pair deletion in the gpX coding region. The S-PRV-155 pseudorabies virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2311.

S-PRY-155 resulted from the removal of the β-galactosidase marker gene from S-PRY-154 (see above). This was accomplished by digestion of S-PRV-154 with XbaI as described in the DIRECT LIGATION PROCEDURE FOR GENERATING RECOMBINANT PRV. The structure of S-PRV-155 was confirmed by restriction enzyme analysis with BamHI and XbaI. The gpX and gI deletions were confirmed by Southern blot analysis with probes for the coding regions of each gene.

The following experiments indicate that S-PRV-155 is useful as a vaccine to protect swine against pseudorabies disease and that it produces an immune response which can be distinguished from wild-type infection.

In this study, three-day-old piglets were vaccinated intramuscularly with S-PRV-155 as follows: 6 were inoculated with $10^3$ PFU, 8 were inoculated with $10^5$ PFU, and 20 were inoculated with $10^{3.5}$ PFU of virus.

Two control groups of 5 each were also included in the study. The animals were observed, then challenged as described in VACCINATION STUDIES WITH SWINE (see Table II below).

distinguished from animals infected with wild-type virus by a simple serum diagnostic assay.

Example 5

TABLE II

VACCINATION OF 3-DAY-OLD PIGLETS WITH S-PRV-155 AND CHALLENGE WITH VIRULENT PRV

| Virus Conc. | No. of Pigs | SN Antibody[a] Post Vaccination | Post Challenge | Post-Vaccination Diagnostic Antibody[b] gpX[c] | gpI[c] | gpI[d] | Post-Challenge Diagnostic Antibody gpX[c] | gpI[c] | gpI[d] | Post-Challenge Observations Virus Shedding[g] | Clinical Signs | Death |
|---|---|---|---|---|---|---|---|---|---|---|---|---|
| $10^3$ pfu per Dose | 6 | 7 | 50 | 0 | 0 | 0 | 67%[e] | NT | 16% | 21% | 0 | 0 |
| $10^5$ pfu per Dose | 8 | 5 | 60 | 0 | 0 | 0 | 62% | NT | 37% | 12% | 0 | 0 |
| None | 5 | <2 | 25 | 0 | 0 | 0 | 100% | NT | 100% | 50% | 100% | 0 |
| $10^{3.5}$ pfu per Dose | 20 | 4 | 316 | 0 | 0 | 0 | 90%[f] | 100% | 100% | 34% | 0 | 0 |
| None | 5 | <2 | 24 | 0 | 0 | 0 | 100% | 100% | 100% | 73% | 100% | 80% |

[a]Geometric mean titer (reciprocal of dilution)
[b]Day of challenge
[c]HerdChek test; percent positive
[d]ClinEase test; percent positive
[e]Day 14 post-challenge
[f]Day 21 post-challenge
[g]Percent of nasal secretion samples positive for virus In this experiment, all of the vaccinated animals remained healthy following vaccination, developed serum neutralizing antibody to PRV and did not shed vaccine virus in tonsillar secretions. After challenge with virulent virus, v the place of the gpI gene and is under the control of the HCMV immediate early promoter.

S-PRV-158 was derived from S-PRV-000 (PRV strain ISU S62/26) through the construction of two intermediate viruses. The first intermediate virus was S-PRV-156. In the first intermediate virus S-PRV-156, the gpX deletion was introduced along with the β-galactosidase (lacZ) marker gene. This was accomplished utilizing the homology vector 436-86.32K (see Materials and Methods) and virus S-PRV-000 in the HOMOLOGOUS RECOMBINATION PROCEDURE FOR GENERATING RECOMBINANT PRV. In the second intermediate virus (S-PRY-157) the β-galactosidase marker gene (lacZ) was removed by digestion with XbaI as described in the DIRECT LIGATION PROCEDURE FOR GENERATING RECOMBINANT PRV. Finally, S-PRV-158 was generated utilizing the homology vector 416-09.2H (see Materials and Methods) and virus S-PRV-157 in the HOMOLOGOUS RECOMBINATION PROCEDURE FOR GENERATING RECOMBINANT PRY. The structure of S-PRV-158 was confirmed by restriction enzyme analysis with BamHI and XbaI.

Example 7

S-PRY-159

S-PRV-159 is a pseudorabies virus that has a 1460 base pair deletion in the gI coding region and a 1414 base pair deletion in the gpX coding region.

S-PRV-159 resulted from the removal of the marker gene from S-PRV-158 (see above). This was accomplished by digestion of S-PRV-158 with XbaI as described in the DIRECT LIGATION PROCEDURE FOR GENERATING RECOMBINANT PRV. The structure of S-PRV-159 was confirmed by restriction enzyme analysis with BamHI and XbaI.

Summary of Examples

The present invention involves the use of genetically engineered herpesviruses to protect animals against disease. These viruses incorporate the deletion of two glycoproteins, gpX and gI. Table IV summarizes characteristics of the six deletion viruses described here. Virus titers were determined according to the TITRATION OF PRV. The safety and efficacy data were generated according to the VACCINATION STUDIES IN SWINE.

TABLE IV

CHARACTERISTICS OF PRV gpX gI DELETION VIRUSES

| | | | Post Challenge Observations | |
|---|---|---|---|---|
| Virus # | Titer pfu/ml | Post Vaccination Clinical Signs | Clinical Signs | Death |
| S-PRV-150 | $2.30 \times 10^6$ | NT | NT | NT |
| S-PRV-151 | $3.80 \times 10^5$ | NONE | 100% | 20% |
| S-PRV-154 | $1.53 \times 10^8$ | NT | NT | NT |
| S-PRV-155 | $1.48 \times 10^8$ | NONE | 0% | 0% |
| S-PRV-158 | $1.47 \times 10^8$ | NT | NT | NT |
| S-PRV-159 | $5.61 \times 10^8$ | NT | NT | NT |

All six viruses incorporate deletions of gpX and gI. The region of the gpX deletion in S-PRV-150 and S-PRV-151 is larger than the gpX deletion in the other viruses. Viruses S-PRV-150, S-PRV-151, S-PRV-154, and S-PRV-155 also have deletions in the TK and the repeat regions. The *E-coli* βB-galactosidase (lacZ) marker gene is present in viruses S-PRV-150, S-PRV-154, and S-PRV-158.

From this analysis it is clear that the precise size and combination of deletions is important to the efficacy of a differential vaccine incorporating both gpX and gI markers. S-PRV-150 and S-PRV-151 exhibit significantly reduced virus titers. The titer to which virus may be grown in cell culture is critical to the manufacture of vaccine. The low titers of S-PRV-150 and S-PRV-151 would make their manufacture as vaccines cost prohibitive. S-PRV-155 and S-PRV-151 also differ dramatically in their ability to protect swine from PRV disease. S-PRV-151 provides an unacceptable level of protection, whereas S-PRV-155 provides complete protection. The combination of deletions present in S-PRV-155 is responsible for making this virus strain a superior vaccine product. This product provides safety in three-day-old piglets, protection in all age pigs, and serologic differentiation using either one or two diagnostic markers. Based on the current state of the art, the superior utility of this combination of deletions was unexpected. These results are novel, unpredictable, and useful in the selection of a superior pseudorabies vaccine product.

References

1. F. L. Graham and A. Van der Eb., Virology 52, 556–567, 1973.
2. T. Maniatis, et al., Molecular Cloning: A Laboratory Manual, Cold Spring Harbor Press, 1982.
3. M. van Zijl, et al., J. of Virology 71, 1747–1755, 1990.
4. T. J. Rea, et al., J. of Virology 54, 21–29, 1985.
5. E. A. Petrovskis, et al., J. of Virology 59, 216–223, 1986.
6. E. A. Petrovskis, et al., J. of Virology 60, 185–193, 1986.
7. E. A. Petrovskis, et al., J. of Virology 60, 1166–1169, 1986.
8. T. Ben-Porat and A. S. Kaplan, Virology 41, 265–273, 1970.
9. T. Ben-Porat, et al., J. of Virology 49, 970–979, 1984.
10. T. Ben-Porat, et al., Virology 154, 325–334, 1986.
11. F. A. Ferrari, et al., J. of Bacteriology 161, 556–562, 1985.
12. D. R. Thomsen, et al., Gene 16, 207–216, 1981.
13. R. W. Price and A. Kahn, Infection and Immunity 34, 571–580, 1981.
14. P. B. Tenser, et al., J. of General Virology 64, 1369–1373, 1983.
15. B. Lomniczi, et al., J. of Virology 49, 970–979, 1984.
16. B. Roizman, et al., Cold Spring Harbor Conference on New Approaches to Viral Vaccines, September, 1983.
17. R. L. Thompson, et al., Virology 131, 180–192, 1983.
18. K. Fukuchi, et al., Proc. Natl. Acad. Sci. U.S.A. 82, 751–754, 1985.
9. J. M. Koomey, et al., J. of Virology 50, 662–665, 1984.
20. M. W. Ligas and D. C. Johnson, J. of Virology 62, 1486–1494, 1988.
21. F. Zuckerman, et al., Vaccination and Control of Adjeszky's Disease, pp. 107–117, Ed. J. van Oirschot. Kluwer, London, 1989.
22. T. C. Mettenleiter, et al., Virology 158, 141–146, 1987.
23. A. K. Robbins, et al., J. of Virology 58, 339–347, 1986.
24. A. K. Robbins, et al., J. of Virology 61, 2691–2701, 1987.

25. L. E. Post, et al., J. Reprod. Fert. Suppl. 41, 97–104, 1990.

---

What we claim is:

1. An attenuated, genetically-engineered pseudorabies virus designated S-PRV-155 (ATCC Accession No. VR 2311).

2. A method of distinguishing an animal vaccinated with a vaccine, said vaccine comprising an attenuated, genetically-engineered pseudorabies virus designated S-PRV-155 (ATCC Accession No. VR 2311), from an animal infected with a naturally-occurring, wild-type pseudorabies virus which comprises detecting the presence or absence of pseudorabies virus glycoprotein X in a body fluid of the animal.

3. The method of claim 2, wherein the presence or absence of the glycoprotein X in the body fluid is determined by detecting in the body fluid antibodies specific for the glycoprotein X.

4. The method of claim 2, wherein the method further comprises detecting the presence or absence of pseudorabies glycoprotein I in the body fluid of the animal.

5. The method of claim 2, wherein the animal is a swine.

6. A method of distinguishing an animal vaccinated with a vaccine, said vaccine comprising an attenuated, genetically-engineered pseudorabies virus designated S-PRV-155 (ATCC Accession No. VR 2311), from an animal infected with a naturally-occurring, wild-type pseudorabies virus which comprises detecting the presence or absence of the glycoprotein I in a body fluid the animal.

7. The method of claim 6, wherein the presence or absence of the glycoprotein I in the body fluid is determined by detecting in the body fluid antibodies specific for the glycoprotein I.

8. The method of claim 6, wherein the animal is a swine.

* * * * *